(12) United States Patent
Butora et al.

(10) Patent No.: US 7,589,085 B2
(45) Date of Patent: Sep. 15, 2009

(54) TETRAHYDROPYRAN HETEROCYCLIC CYCLOPENTYL HETEROARYL MODULATORS OF CHEMOKINE RECEPTOR ACTIVITY

(75) Inventors: Gabor Butora, Martinsville, NJ (US); Lihu Yang, Edison, NJ (US); Stephen D. Goble, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 675 days.

(21) Appl. No.: 10/567,516

(22) PCT Filed: Aug. 6, 2004

(86) PCT No.: PCT/US2004/025467

§ 371 (c)(1),
(2), (4) Date: Feb. 7, 2006

(87) PCT Pub. No.: WO2005/014537

PCT Pub. Date: Feb. 17, 2005

(65) Prior Publication Data

US 2006/0205783 A1   Sep. 14, 2006

Related U.S. Application Data

(60) Provisional application No. 60/493,902, filed on Aug. 8, 2003.

(51) Int. Cl.
*C07D 401/02* (2006.01)
*A61K 31/44* (2006.01)
(52) U.S. Cl. .................. 514/217.04; 514/336; 540/481; 540/597; 546/282.1
(58) Field of Classification Search ........................ None
See application file for complete search history.

(56) References Cited

U.S. PATENT DOCUMENTS

| 4,048,180 | A | 9/1977 | Bowden |
| 6,545,023 | B2 | 4/2003 | Yang et al. |

FOREIGN PATENT DOCUMENTS

| WO | WO 2004/041161 A2 | 5/2004 |
| WO | WO 2004/110376 A2 | 12/2004 |
| WO | WO 2005/120505 A2 | 12/2005 |

OTHER PUBLICATIONS

European Search Report (Supplementary); Performed by: The Hague; Date of Completion: Jan. 30, 2009; Performed by authorized Examiner: Elia Bonnevalle.

*Primary Examiner*—Zinna N Davis
(74) *Attorney, Agent, or Firm*—Mark R. Daniel; James L. McGinnis

(57) ABSTRACT

The present invention is further directed to compounds of the formulas: (I) (II) (wherein $R^1$, $R^2$, $R^3$, $R^4$, $R^5$, $R^6$, $R^7$, $R^8$, $R^9$, $R^{10}$, $R^{15}$, $R^{16}$, $R^{17}$, $R^{18}$, $R^{19}$, $R^{24}$ and $R^{25}$ are as defined herein) which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

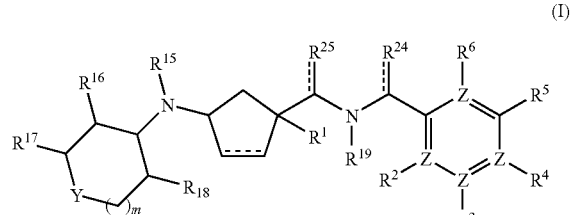

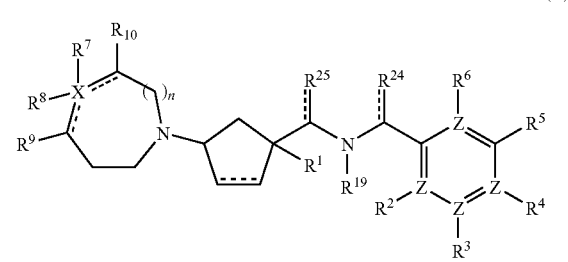

42 Claims, No Drawings

US 7,589,085 B2

TETRAHYDROPYRAN HETEROCYCLIC CYCLOPENTYL HETEROARYL MODULATORS OF CHEMOKINE RECEPTOR ACTIVITY

Related Application Data

This is a National filing under 35 USC 371 of PCT/US2004/025467, filed Aug. 6, 2004, which claims priority from U.S. Ser. No. 60/493,902, filed Aug. 8, 2003.

BACKGROUND OF THE INVENTION

The chemokines are a family of small (70-120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, *Cytokine,* 3, 165-183 (1991) and Murphy, *Rev. Immun.,* 12, 593-633 (1994)). These molecules were originally defined by four conserved cysteines and divided into two subfamilies based on the arrangement of the first cysteine pair. In the CXC-chemokine family, which includes IL-8, GROα, NAP-2 and IP-10, these two cysteines are separated by a single amino acid, while in the CC-chemokine family, which includes RANTES, MCP-1, MCP-2, MCP-3, MIP-1α, MIP-1β and eotaxin, these two residues are adjacent.

The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, monocytes, T-cells, eosinophils and basophils (Deng, et al., *Nature,* 381, 661-666 (1996)).

The chemokines are secreted by a wide variety of cell types and bind to specific G-protein coupled receptors (GPCRs) (reviewed in Horuk, *Trends Pharm. Sci.,* 15, 159-165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.,* 270, 22123-22128 (1995); Beote, et al, *Cell,* 72, 415-425 (1993)); CCR-2A and CCR-2B (or "CKR-2"/"CKR-2A" or "CC-CKR-2A"/"CC-CKR-2A") [MCP-1, MCP-2, MCP-3, MCP-4]; CCR-3 (or "CKR-3" or "CC-CKR-3") [Eotaxin, Eotaxin 2, RANTES, MCP-2, MCP-3] (Rollins, et al., *Blood,* 90, 908-928 (1997)); CCR-4 (or "CKR-4" or "CC-CKR-4") [MIP-1α, RANTES, MCP-1] (Rollins, et al., *Blood,* 90, 908-928 (1997)); CCR-5 (or "CKR-5" or "CC-CKR-5") [MIP-1α, RANTES, MIP-1β] (Sanson, et al., *Biochemistry,* 35, 3362-3367 (1996)); and the Duffy blood-group antigen [RANTES, MCP-1] (Chaudhun, et al., *J. Biol. Chem.,* 269,7835-7838 (1994)). The β-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., *Arthritis & Rheumatism,* 42, 989-992 (1999)). A review of the role of eosinophils in allergic inflammation is provided by Kita, H., et al., *J. Exp. Med.* 183, 2421-2426 (1996). A general review of the role of chemokines in allergic inflammation is provided by Lustger, A. D., *New England J. Med.,* 338(7), 426-445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and *Listeria monocytogenes* infection (Lu et al., *J. Exp. Med.,* 187, 601-608 (1998); Kurihara et al. *J. Exp. Med.,* 186, 1757-1762 (1997); Boring et al. *J. Clin. Invest.,* 100, 2552-2561 (1997); Kuziel et al. *Proc. Natl. Acad. Sci.,* 94, 12053-12058 (1997)). Furthermore, these animals show reduced monocyte infiltration into granulomatous lesions induced by the injection of schistosomal or mycobacterial antigens (Boring et al. *J. Clin. Invest.,* 100, 2552-2561 (1997); Warmington et al. *Am J. Path.,* 154, 1407-1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases.

Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1-/- or CCR2-/- mice backcrossed to APO-E-/-, LDL-R-/- or Apo B transgenic mice maintained on high fat diets (Boring et al. *Nature,* 394, 894-897 (1998); Gosling et al. *J. Clin. Invest.,* 103, 773-778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is further directed to compounds of formulae I and II:

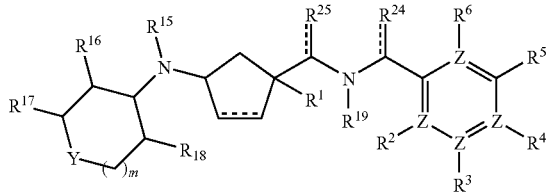

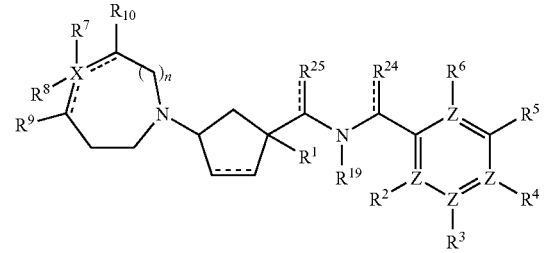

(wherein $R^1$, $R^2$, $R^3$, $R^4$, $R^5$, $R^6$, $R^7$, $R^8$, $R^9$, $R^{10}$, $R^{15}$, $R^{16}$, $R^{17}$, $R^{18}$, $R^{19}$, $R^{24}$ and $R^{25}$ are as defined herein) which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of Formulae I and II:

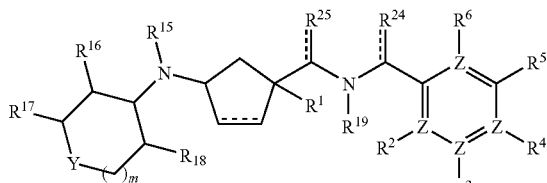

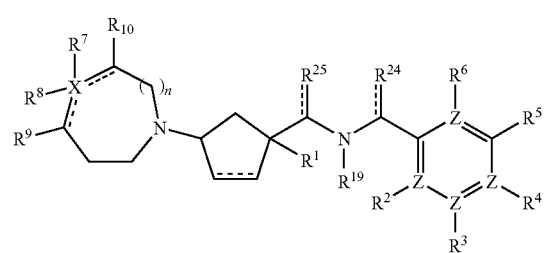

wherein:
X is selected from O, N, S, $SO_2$ and C;
Y is selected from —O—, —$NR^{12}$—, —S—, —SO—, —$SO_2$—, and —$CR^{12}R^{12}$—, —$NSO_2R^{14}$—, —$NCOR^{13}$—, —$CR^{12}COR^{11}$—, —$CR^{12}OCOR^{13}$—, —CO—;

Z is independently selected from C or N, where at least one Z is N and at most two Z are N;
$R^1$ is selected from: —$C_{1-6}$alkyl, —$C_{0-6}$alkyl-O—$C_{1-6}$alkyl, —$C_{0-6}$alkyl-S—$C_{1-6}$alkyl, —($C_{0-6}$alkyl)-($C_{3-7}$cycloalkyl)-($C_{0-6}$alkyl), hydroxy, heterocycle, —CN, —$NR^{12}R^{12}$, —$NR^{12}COR^{13}$, —$NR^{12}SO_2R^{14}$, —$COR^{11}$, —$CONR^{12}R^{12}$, phenyl, and pyridyl,
where the alkyl and the cycloalkyl are unsubstituted or substituted with 1-7 substituents independently selected from: halo, hydroxy, —O—$C_{1-3}$alkyl, trifluoromethyl, $C_{1-3}$alkyl, —O—$C_{1-3}$alkyl, —$COR^{11}$, —$SO_2R^{14}$, —$NHCOCH_3$, —$NHSO_2CH_3$, -heterocycle, =O, —CN,
where the phenyl and pyridyl are unsubstituted or substituted with 1-3 substituents where the substituents are independently selected from: halo, hydroxy, $COR^{11}$, $C_{1-3}$alkyl, $C_{1-3}$alkoxy and trifluoromethyl,
where $R^{11}$ is independently selected from: hydroxy, hydrogen, $C_{1-6}$ alkyl, —O—$C_{1-6}$alkyl, benzyl, phenyl and $C_{3-6}$ cycloalkyl, where the alkyl, phenyl, benzyl, and cycloalkyl groups are unsubstituted or substituted with 1-3 substituents independently selected from: halo, hydroxy, $C_{1-3}$alkyl, $C_{1-3}$alkoxy, —$CO_2H$, —$CO_2$—$C_{1-6}$alkyl, and trifluoromethyl,
where $R^{12}$ is selected from: hydrogen, $C_{1-6}$ alkyl, benzyl, phenyl and $C_{3-6}$ cycloalkyl, where the alkyl, phenyl, benzyl, and cycloalkyl groups are unsubstituted or substituted with 1-3 substituents independently selected from:
halo, hydroxy, $C_{1-3}$alkyl, $C_{1-3}$alkoxy, —$CO_2H$, —$CO_2$—$C_{1-6}$alkyl, and trifluoromethyl,
where $R^{13}$ is selected from: hydrogen, $C_{1-6}$ alkyl, —O—$C_{1-6}$alkyl, benzyl, phenyl and $C_{3-6}$ cycloalkyl, where the alkyl, phenyl, benzyl, and cycloalkyl groups are unsubstituted or substituted with 1-3 substituents independently selected from:
halo, hydroxy, $C_{1-3}$alkyl, $C_{1-3}$alkoxy, —$CO_2H$, —$CO_2$—$C_{1-6}$alkyl, and trifluoromethyl, and
where $R^{14}$ is selected from: hydroxy, $C_{1-6}$ alkyl, —O—$C_{1-6}$ alkyl, benzyl, phenyl and $C_{3-6}$ cycloalkyl, where the alkyl, phenyl, benzyl, and cycloalkyl groups are unsubstituted or substituted with 1-3 substituents independently selected from:
halo, hydroxy, $C_{1-3}$alkyl, $C_{1-3}$alkoxy, —$CO_2H$, —$CO_2$—$C_{1-6}$ alkyl, and trifluoromethyl;
$R^2$ is selected from: hydrogen, $C_{1-3}$alkyl, unsubstituted or substituted with 1-3 fluoro, —O—$C_{1-6}$alkyl, unsubstituted or substituted with 1-3 fluoro, hydroxy, chloro, fluoro, bromo, phenyl, heterocycle, and nothing, and O, when the Z bonded to $R^2$ is N;
$R^3$ is selected from: hydrogen, $C_{1-3}$alkyl, unsubstituted or substituted with 1-3 fluoro, —O—$C_{1-3}$alkyl, unsubstituted or substituted with 1-3 fluoro, hydroxy, chloro, fluoro, bromo, phenyl, heterocycle, and nothing, and O, when the Z bonded to $R^2$ is N;
$R^4$ is selected from: hydrogen, $C_{1-3}$alkyl, unsubstituted or substituted with 1-3 fluoro, —O—$C_{1-3}$alkyl, unsubstituted or substituted with 1-3 fluoro, hydroxy, chloro, fluoro, bromo, phenyl, heterocycle, and nothing, and O, when the Z bonded to $R^2$ is N;
$R^5$ is selected from: $C_{1-6}$alkyl, unsubstituted or substituted with 1-6 substituents selected from fluoro and hydroxyl, —O—$C_{1-6}$alkyl, unsubstituted or substituted with 1-6 fluoro, —CO—$C_{1-6}$alkyl, unsubstituted or substituted with 1-6 fluoro, —S—$C_{1-6}$alkyl, unsubstituted or substituted with 1-6 fluoro, -pyridyl, unsubstituted or substituted with one or more substituents selected from: halo, trifluoromethyl, $C_{1-4}$alkyl, and $COR^{11}$, fluoro, chloro, bromo, —$C_{4-6}$cycloalkyl, —O—$C_{4-6}$cycloalkyl, phenyl, unsubstituted or substituted with one or more substituents selected from:
halo, trifluoromethyl, $C_{1-4}$alkyl, and $COR^{11}$, —O-phenyl, unsubstituted or substituted with one or more substituents selected from: halo, trifluoromethyl, $C_{1-4}$alkyl, and $COR^{11}$, —$C_{3-6}$cycloalkyl, unsubstituted or substituted with 1-6 fluoro, —O—$C_{3-6}$cycloalkyl, unsubstituted or substituted with 1-6 fluoro, -heterocycle, —CN, and —$COR^{11}$;

$R^6$ is selected from: hydrogen, $C_{1-3}$alkyl, unsubstituted or substituted with 1-3 fluoro, —O—$C_{1-3}$alkyl, unsubstituted or substituted with 1-3 fluoro, hydroxy, chloro, fluoro, bromo, phenyl, heterocycle, and nothing, and O, when the Z bonded to $R^2$ is N;

$R^7$ is selected from: hydrogen, $(C_{0-6}$alkyl$)$-phenyl, $(C_{0-6}$alkyl$)$-heterocycle, $(C_{0-6}$alkyl$)$-$C_{3-7}$cycloalkyl, $(C_{0-6}$alkyl$)$-$COR^{11}$, $(C_{0-6}$alkyl$)$-(alkene)-$COR^{11}$, $(C_{0-6}$alkyl$)$-$SO_3H$, $(C_{0-6}$alkyl$)$-W —$C_{0-4}$alkyl, $(C_{0-6}$alkyl$)$-$CONR^{12}$-phenyl, $(C_{0-6}$alkyl$)$-$CONR^{20}$—V—$COR^{11}$, and nothing, when X is O, S, or $SO_2$,
where W is selected from: a single bond, —O—, —S—, —SO—, —$SO_2$—, —CO—, —$CO_2$—, —$CONR^{12}$— and —$NR^{12}$—,
where V is selected from $C_{1-6}$alkyl or phenyl,
where $R^{20}$ is hydrogen or $C_{1-4}$alkyl, or where $R^{20}$ is joined via a 1-5 carbon tether to one of the carbons of V to form a ring,
where the $C_{0-6}$alkyl is unsubstituted or substituted with 1-5 substituents independently selected from:
halo, hydroxy, —$C_{0-6}$alkyl, —O—$C_{1-3}$alkyl, trifluoromethyl, and —$C_{0-2}$alkyl-phenyl,
where the phenyl, heterocycle, cycloalkyl, and $C_{0-4}$alkyl is unsubstituted or substituted with 1-5 substituents independently selected from: halo, trifluoromethyl, hydroxy, $C_{1-3}$alkyl, —O—$C_{1-3}$alkyl, —$C_{0-3}$—$COR^{11}$, —CN, —$NR^{12}R^{12}$, —$CONR^{12}R^{12}$, and —$C_{0-3}$-heterocycle, or
where the phenyl and heterocycle may be fused to another heterocycle, which itself may be unsubstituted or substituted with 1-2 substituents independently selected from hydroxy, halo, —$COR^{11}$, and —$C_{1-3}$alkyl, and
where alkene is unsubstituted or substituted with 1-3 substituents which are independently selected from: halo, trifluoromethyl, $C_{1-3}$alkyl, phenyl, and heterocycle;

$R^8$ is selected from: hydrogen, nothing when X is either O, S, $SO_2$ or N or when a double bond joins the carbons to which $R^7$ and $R^{10}$ are attached, hydroxy, $C_{1-6}$alkyl, $C_{1-6}$alkyl-hydroxy, —O—$C_{1-3}$alkyl, —$COR^{11}$, —$CONR^{12}R^{12}$, and —CN;
where $R^7$ and $R^8$ may be joined together to form a ring selected from:
1H-indene, 2,3-dihydro-1H-indene, 2,3-dihydro-benzofuran, 1,3-dihydro-isobenzofuran, 2,3-dihydro-benzothiofuran, 1,3-dihydro-isobenzothiofuran, 6H-cyclopenta[d]isoxazol-3-ol, cyclopentane, and cyclohexane,
where the ring formed is unsubstituted or substituted with 1-5 substituents independently selected from: halo, trifluoromethyl, hydroxy, $C_{1-3}$alkyl, —O—$C_{1-3}$alkyl, —$C_{0-3}$—$COR^{11}$, —CN, —$NR^{12}R^{12}$, —$CONR^{12}R^{12}$, and —$C_{0-3}$-heterocycle, or
where $R^7$ and $R^9$ or $R^8$ and $R^{10}$ may be joined together to form a ring which is phenyl or heterocycle,
wherein the ring is unsubstituted or substituted with 1-7 substituents where the substituents are independently selected from: halo, trifluoromethyl, hydroxy, $C_{1-3}$alkyl, —O—$C_{1-3}$alkyl, —$COR^{11}$, —CN, —$NR^{12}R^{12}$, and —$CONR^{12}R^{12}$;

$R^9$ and $R^{10}$ are independently selected from: hydrogen, hydroxy, $C_{1-6}$alkyl, $C_{1-6}$alkyl-$COR^{11}$, $C_{1-6}$alkyl-hydroxy, —O—$C_{1-3}$alkyl, =O, when $R^9$ or $R^{10}$ is connected to the ring via a double bond, and halo;

$R^{15}$ is selected from: hydrogen, and $C_{1-6}$alkyl, unsubstituted or substituted with 1-3 substituents independently selected from: halo, hydroxy, —$CO_2H$, —$CO_2C_{1-6}$alkyl, and —O—$C_{1-3}$alkyl;

$R^{16}$ is selected from: hydrogen, $C_{1-6}$alkyl, unsubstituted or substituted with 1-6 substituents selected from: fluoro, $C_{1-3}$alkoxy, hydroxyl and —$COR^{11}$, fluoro, —O—$C_{1-3}$alkyl, unsubstituted or substituted with 1-3 fluoro, $C_{3-6}$cycloalkyl, —O—$C_{3-6}$cycloalkyl, hydroxy, —COR11, and —$OCOR^{13}$, or $R^{15}$ and $R^{16}$ are joined together via a $C_{2-4}$alkyl or a $C_{0-2}$alkyl-O—$C_{1-3}$alkyl chain to form a 5-7 membered ring;

$R^{17}$ is selected from: hydrogen, $C_{1-6}$alkyl, unsubstituted or substituted with 1-6 substituents selected from: fluoro, $C_{1-3}$alkoxy, hydroxyl and —$COR^{11}$, $COR^{11}$, hydroxy, and —O—$C_{1-6}$alkyl, unsubstituted or substituted with 1-6 substituents selected form: fluoro, $C_{1-3}$alkoxy, hydroxy, and —$COR^{11}$, or $R^{16}$ and $R^{17}$ may be joined together by a $C_{1-4}$alkyl chain or a $C_{0-3}$alkyl-O—$C_{0-3}$alkyl chain to form a 3-6 membered ring;

$R^{18}$ is selected from: hydrogen, $C_{1-6}$alkyl, unsubstituted or substituted with 1-6 fluoro, fluoro, —O—$C_{3-6}$cycloalkyl, and —O—$C_{1-3}$alkyl, unsubstituted or substituted with 1-6 fluoro, or $R^{16}$ and $R^{18}$ are joined together by a $C_{2-3}$alkyl chain to form a 5-6 membered ring, where the alkyl are unsubstituted or substituted with 1-3 substituents independently selected from: halo, hydroxy, —$COR^{11}$, $C_{1-3}$alkyl, and $C_{1-3}$alkoxy, or $R^{16}$ and $R^{18}$ are joined together by a $C_{1-2}$alkyl-O—$C_{1-2}$alkyl chain to form a 6-8 membered ring, where the alkyl are unsubstituted or substituted with 1-3 substituents independently selected from: halo, hydroxy, —$COR^{11}$, $C_{1-3}$alkyl, and $C_{1-3}$alkoxy, or $R^{16}$ and $R^{18}$ are joined together by a —O—$C_{1-2}$alkyl-O-chain to form a 6-7 membered ring, where the alkyl are unsubstituted or substituted with 1-3 substituents independently selected from: halo, hydroxy, —$COR^{11}$, $C_{1-3}$alkyl, and $C_{1-3}$alkoxy;

$R^{19}$ is selected from: hydrogen, phenyl, $C_{1-6}$alkyl substituted or unsubstituted with 1-6 substituents selected from: —$COR^{11}$, hydroxy, fluoro, chloro and —O—$C_{1-3}$alkyl;

$R^{24}$ and $R^{25}$ are independently selected from: =O, where one of $R^{24}$ and $R^{25}$ is oxygen bound via a double bond. hydrogen, phenyl, and $C_{1-6}$alkyl, substituted or unsubstituted with 1-6 substituents selected from: —$COR^{11}$, hydroxy, fluoro, chloro, —O—$C_{1-3}$alkyl;

m is 0, 1 or 2;

n is 1 or 2;

the dashed line represents a single or a double bond; and pharmaceutically acceptable salts thereof and individual diastereomers thereof.

Embodiments of the present invention include compounds of formula Ia:

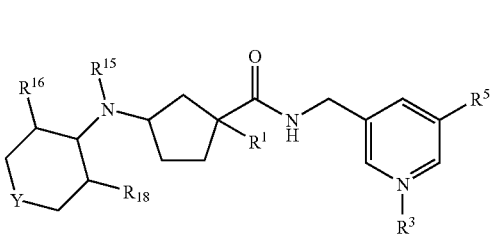

wherein $R^1$, $R^3$, $R^5$, $R^{15}$, $R^{16}$, $R^{18}$ and Y are as described herein, and pharmaceutically acceptable salts and individual diastereomers thereof.

Additional embodiments of the present invention also include compounds of formula IIa:

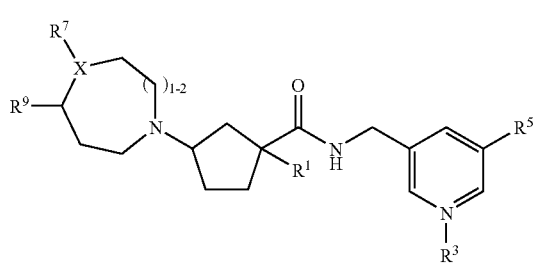

wherein $R^1$, $R^2$, $R^3$, $R^5$, $R^7$, $R^9$, and X are as defined herein, and pharmaceutically acceptable salts and individual diastereomers thereof.

More embodiments of the present invention include compounds of formula Ib:

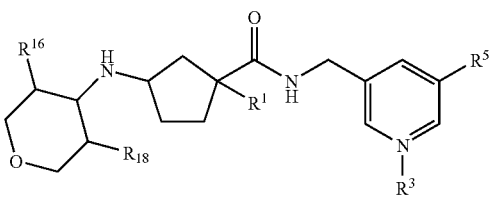

wherein $R^1$, $R^3$, $R^5$, $R^{16}$, and $R^{18}$ are as described herein, and pharmaceutically acceptable salts and individual diastereomers thereof.

More embodiments of the present invention also include those of formula IIb:

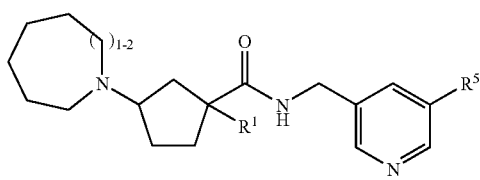

wherein $R^1$ and $R^5$ are as defined herein, and pharmaceutically acceptable salts and individual diastereomers thereof.

Still more embodiments of the present invention include compounds of formula Ic:

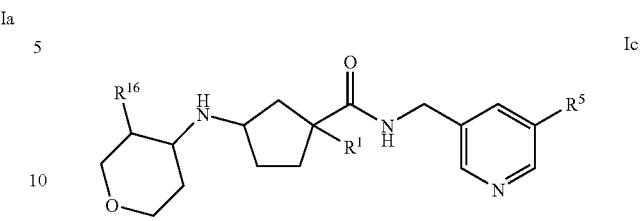

wherein $R^1$, $R^5$, and $R^{16}$ are as described herein, and pharmaceutically acceptable salts and individual diastereomers thereof.

In certain embodiments of the invention X is C, O or N.

In certain other embodiments of the invention X is C.

In certain embodiments of the invention Y is —$CH_2$— or —O—

In certain embodiments of the invention $R^1$ is selected from: —$C_{1-6}$alkyl, —$C_{0-6}$alkyl-O—$C_{1-6}$alkyl, heterocycle, and —($C_{0-6}$alkyl)-($C_{3-7}$cycloalkyl)-($C_{0-6}$alkyl), where the alkyl, heterocycle, and the cycloalkyl are unsubstituted or substituted with 1-7 substituents independently selected from: halo, hydroxy, —O—$C_{1-3}$alkyl, trifluoromethyl, $C_{1-3}$alkyl, —O—$C_{1-3}$alkyl, —$COR^{11}$, —CN, —$NR^{12}R^{12}$, and —$CONR^{12}R^{12}$.

According to other embodiments of the invention $R^1$ is selected from:
- —$C_{1-6}$alkyl, unsubstituted or substituted with 1-6 substituents independently selected from: halo, hydroxy, —O—$C_{1-3}$alkyl, trifluoromethyl, and —$COR^{11}$;
- —$C_{0-6}$alkyl-O—$C_{1-6}$alkyl-, unsubstituted or substituted with 1-6 substituents independently selected from: halo, trifluoromethyl, and —$COR^{11}$; and
- —($C_{3-5}$cycloalkyl)-($C_{0-6}$alkyl), unsubstituted or substituted with 1-7 substituents independently selected from: halo, hydroxy, —O—$C_{1-3}$alkyl, trifluoromethyl, and —$COR^{11}$.

In certain embodiments of the invention $R^1$ is selected from: $C_{1-6}$alkyl, $C_{1-6}$alkyl substituted with hydroxyl, and $C_{1-6}$alkyl substituted with 1-6 fluoro.

In other embodiments of the invention $R^1$ is selected from: —$CH(CH_3)_2$, —$CH(OH)CH_3$, —$C(OH)(CH_3)_2$, and —$CH_2CF_3$.

The invention includes embodiments in which $R^2$ is hydrogen.

The invention includes embodiments in which $R^3$ is nothing.

The invention includes embodiments in which $R^4$ is hydrogen.

The invention includes embodiments in which $R^5$ is selected from: $C_{1-6}$alkyl substituted with 1-6 fluoro, —O—$C_{1-6}$alkyl substituted with 1-6 fluoro, chloro, bromo, and phenyl.

The invention includes embodiments in which $R^5$ is selected from: trifluoromethyl, trifluoromethoxy, chloro, bromo, and phenyl.

The invention includes embodiments in which $R^5$ is trifluoromethyl.

The invention includes embodiments in which $R^6$ is hydrogen.

The invention also includes embodiments in which $R^7$ is selected from phenyl, heterocycle, $C_{3-7}$cycloalkyl, $C_{1-6}$alkyl, —$COR^{11}$, and —CONH—V—$COR^{11}$, where V is selected from $C_{1-6}$alkyl and phenyl, and where the phenyl, heterocycle, $C_{3-7}$cycloalkyl, and $C_{1-6}$alkyl is unsubstituted or substituted with 1-5 substituents independently selected from: halo, trifluoromethyl, hydroxy, $C_{1-3}$alkyl, —O—$C_{1-3}$alkyl, —COR$^{11}$, —CN, -heterocycle, and —CONR$^{12}$R$^{12}$.

Further embodiments of the invention include those in which, when X is not O, R$^7$ is selected from phenyl, heterocycle, $C_{1-4}$alkyl, —COR$^{11}$ and —CONH—V—COR$^{11}$, where V is selected from $C_{1-6}$alkyl or phenyl, where the phenyl, heterocycle, and $C_{1-4}$alkyl is unsubstituted or substituted with 1-3 substituents independently selected from: halo, hydroxy, $C_{1-3}$alkyl, —O—$C_{1-3}$alkyl, —COR$^{11}$, and -heterocycle.

The invention includes embodiments in which when X is O, R$^7$ and R$^8$ are nothing.

The invention includes embodiments in which when X is C, R$^8$ is hydrogen.

The invention includes embodiments in which R$^9$ is selected from: hydrogen, hydroxy, —CH$_3$, —O—CH$_3$, and =O, where R$^9$ is joined to the ring via a double bond.

The invention includes embodiments in which R$^9$ is hydrogen.

The invention includes embodiments in which R$^{10}$ is hydrogen.

The invention includes embodiments in which R$^{15}$ is hydrogen or methyl.

The invention includes embodiments in which R$^{16}$ is selected from: hydrogen, $C_{1-3}$alkyl, unsubstituted or substituted with 1-6 fluoro, —O—$C_{1-3}$alkyl, fluoro, and hydroxy.

The invention includes embodiments in which R$^{16}$ is selected from: hydrogen, trifluoromethyl, methyl, methoxy, ethoxy, ethyl, fluoro, and hydroxy.

The invention includes embodiments in which R$^{17}$ is hydrogen.

The invention includes embodiments in which R$^{18}$ is selected from: hydrogen, methyl, and methoxy.

The invention includes embodiments in which R$^{18}$ is hydrogen.

The invention includes embodiments in which R$^{16}$ and R$^{18}$ are joined together by a —CH$_2$CH$_2$— chain or a —CH$_2$CH$_2$CH$_2$— chain to form a cyclopentyl ring or a cyclohexyl ring.

The invention includes embodiments in which R$^{19}$ is hydrogen.

The invention includes embodiments in which R$^{24}$ is hydrogen.

The invention includes embodiments in which R$^{25}$ is =O, where an oxygen is joined via a double bond.

The invention includes embodiments in which that m=0 or 1.

The invention includes embodiments in which n=1 or 2.

Representative compounds of the present invention include those presented in the Examples and pharmaceutically acceptable salts and individual diastereomers thereof.

The compounds of the instant invention have at least one asymmetric center at the 1 and/or 3 positions of the cyclopentyl ring. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The absolute configurations of selected compounds of this orientation, with substituents on the cyclopentyl ring (amide and amine units), are as depicted below:

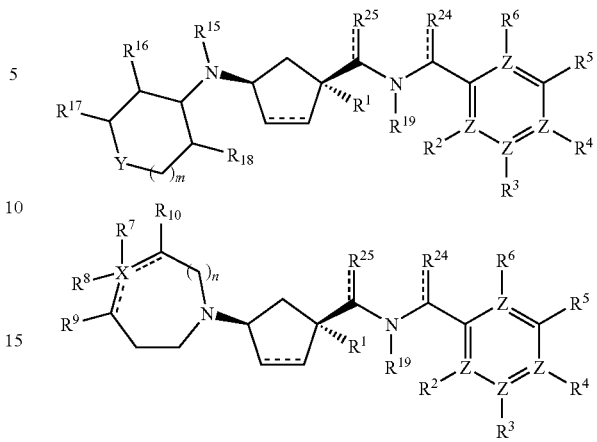

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$alkyl is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. Likewise, $C_0$, as in $C_0$alkyl is defined to identify the presence of a direct covalent bond. The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoim idazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media such as ether, ethyl acetate, ethanol, isopropanol, or acetonitrile are preferred. Suitable salts are found, e.g. in Remington's Pharmaceutical Sciences, 17th ed., Mack Publishing Company, Easton, Pa., 1985, p. 1418.

Exemplifying the invention is the use of the compounds disclosed in the Examples and herein.

Specific compounds within the present invention include a compound which selected from the group consisting of: the title compounds of the Examples; and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, in particular CCR-2.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177 851-856 (1993) which may be readily adapted for measurement of CCR-2 binding.

Receptor affinity in a CCR-2 binding assay was determined by measuring inhibition of $^{125}$I-MCP-1 to the endogenous CCR-2 receptor on various cell types including monocytes, THP-1 cells, or after heterologous expression of the cloned receptor in eukaryotic cells. The cells were suspended in binding buffer (50 mM HEPES, pH 7.2, 5 mM $MgCl_2$, 1 mM $CaCl_2$, and 0.50% BSA or 0.5% human serum) and added to test compound or DMSO and $^{125}$I-MCP-1 at room temperature for 1 h to allow binding. The cells were then collected on GFB filters, washed with 25 mM HEPES buffer containing 500 mM NaCl and cell bound $^{125}$I-MCP-1 was quantified.

In a chemotaxis assay chemotaxis was performed using T cell depleted PBMC isolated from venous whole or leukophoresed blood and purified by Ficoll-Hypaque centrifugation followed by rosetting with neuraminidase-treated sheep erythrocytes. Once isolated, the cells were washed with HBSS containing 0.1 mg/ml BSA and suspended at $1\times10^7$ cells/ml. Cells were fluorescently labeled in the dark with 2 μM Calcien-AM (Molecular Probes), for 30 min at 37° C. Labeled cells were washed twice and suspended at $5\times10^6$ cells/ml in RPMI 1640 with L-glutamine (without phenol red) containing 0.1 mg/ml BSA. MCP-1 (Peprotech) at 10 ng/ml diluted in same medium or medium alone were added to the bottom wells (27 μl). Monocytes (150,000 cells) were added to the topside of the filter (30 μl) following a 15 min preincubation with DMSO or with various concentrations of test compound. An equal concentration of test compound or DMSO was added to the bottom well to prevent dilution by diffusion. Following a 60 min incubation at 37° C., 5% $CO_2$, the filter was removed and the topside was washed with HBSS containing 0.1 mg/ml BSA to remove cells that had not migrated into the filter. Spontaneous migration (chemokinesis) was determined in the absence of chemoattractant In particular, the compounds of the following examples had activity in binding to the CCR-2 receptor in the aforementioned assays, generally with an $IC_{50}$ of less than about 1 μM. Such a result is indicative of the intrinsic activity of the compounds in use as modulators of chemokine receptor activity.

Mammalian chemokine receptors provide a target for interfering with or promoting eosinophil and/or leukocyte function in a mammal, such as a human. Compounds which inhibit or promote chemokine receptor function, are particularly useful for modulating eosinophil and/or leukocyte function for therapeutic purposes. Accordingly, compounds which inhibit or promote chemokine receptor function would be useful in treating, preventing, ameliorating, controlling or reducing the risk of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis, and further, chronic obstructive pulmonary disease, and multiple schlerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the compounds of the present invention. In a certain embodiment, the disease or condition is one in which the actions of leukocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; and cancers, including cancers with leukocyte infiltration of the skin or organs and other cancers. Inhibitors of chemokine receptor function may also be useful in the treatment and prevention of stroke (Hughes et al., *Journal of Cerebral Blood Flow & Metabolism,* 22:308-317, 2002, and Takami et al., *Journal of Cerebral Blood Flow & Metabolism,* 22:780-784, 2002), neurodegenerative conditions including but not limited to Alzheimer's disease, amyotrophic lateral sclerosis (ALS) and Parkinson's disease, obesity, type II diabetes, neuropathic and inflammatory pain, and Guillain Barre syndrome. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis and chronic obstructive pulmonary disease.

Diseases or conditions of humans or other species, which can be treated with modulators of chemokine receptor function, include or involve but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms), (*Trichuriasis, Enterobiasis, Ascariasis,* Hookworm, *Strongyloidiasis, Trichinosis, filariasis*), trematodes (flukes) (*Schistosomiasis, Clonorchiasis*), cestodes (tape worms) (*Echinococcosis, Taeniasis saginata, Cysticercosis*), visceral worms, visceral larva migraines (e.g., *Toxocara*), eosinophilic gastroenteritis (e.g., *Anisaki* sp., *Phocanema* sp.), and cutaneous larva migraines (*Ancylostona braziliense, Ancylostoma caninum*).

In addition, treatment of the aforementioned inflammatory, allergic, infectious and autoimmune diseases can also be contemplated for agonists of chemokine receptor function if one contemplates the delivery of sufficient compound to cause the loss of receptor expression on cells through the induction of chemokine receptor internalization or delivery of compound in a manner that results in the misdirection of the migration of cells.

The compounds of the present invention are accordingly useful in treating, preventing, ameliorating, controlling or reducing the risk of a wide variety of inflammatory and immunoregulatory disorders and diseases, allergic conditions, atopic conditions, as well as autoimmune pathologies. In a specific embodiment, the present invention is directed to the use of the subject compounds for treating, preventing, ameliorating, controlling or reducing the risk of autoimmune diseases, such as rheumatoid arthritis, psoriatic arthritis and multiple schlerosis.

In another aspect, the instant invention may be used to evaluate putative specific agonists or antagonists of chemokine receptors, including CCR-2. Accordingly, the present invention is directed to the use of these compounds in the preparation and execution of screening assays for compounds that modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-2. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of the present compounds in treating, preventing, ameliorating, controlling or reducing the risk of infection by a retrovirus, in particular, herpes virus or the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a further aspect of the present invention, a subject compound may be used in a method of inhibiting the binding of a chemokine to a chemokine receptor, such as CCR-2, of a target cell, which comprises contacting the target cell with an amount of the compound which is effective at inhibiting the binding of the chemokine to the chemokine receptor.

The subject treated in the methods above is a mammal, for instance a human being, male or female, in whom modulation of chemokine receptor activity is desired. "Modulation" as used herein is intended to encompass antagonism, agonism, partial antagonism, inverse agonism and/or partial agonism. In an aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

As used herein, the term "treatment" refers both to the treatment and to the prevention or prophylactic therapy of the aforementioned conditions.

Combined therapy to modulate chemokine receptor activity for thereby treating, preventing, ameliorating, controlling or reducing the risk of inflammatory and immunoregulatory disorders and diseases, including asthma and allergic diseases, as well as autoimmune pathologies such as rheumatoid arthritis and multiple sclerosis, and those pathologies noted above is illustrated by the combination of the compounds of this invention and other compounds which are known for such utilities.

For example, in treating, preventing, ameliorating, controlling or reducing the risk of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, biological TNF sequestrants, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with CCR2 antagonists, such as the CCR2 antagonists compounds of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin, EDG receptor agonists including FTY-720, and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (e) non-steroidal anti-asthmatics such as $\beta$2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3, CXCR-3, CXCR-4 and CCR-5; (j) cholesterol lowering agents such as HMG-CoA reductase inhibitors (lovastatin, simvastatin and pravastatin, fluvastatin, atorvastatin, rosuvastatin, and other statins), sequestrants (cholestyramine and colestipol), cholesterol absorption inhibitors (ezetimibe), nicotinic acid, fenofibric acid derivatives (gemfibrozil, clofibrat, fenofibrate and benzafibrate), and probucol; (k) antidiabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) preparations of glatiramer acetate; (n) preparations of CTLA4Ig; (o) preparations of hydroxychloroquine, (p) Copaxone® and (q) other compounds such as 5-aminosalicylic acid and prodrugs thereof, antimetabolites such as azathioprine, 6-mercaptopurine and methotrexate, leflunomide, teriflunomide, and cytotoxic and other cancer chemotherapeutic agents.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, or from about 200:1 to about 1:200.

Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In treating, preventing, ameliorating, controlling or reducing the risk of conditions which require chemokine receptor modulation an appropriate dosage level will generally be about 0.0001 to 500 mg per kg patient body weight per day which can be administered in single or multiple doses. In certain embodiments the dosage level will be about 0.0005 to about 400 mg/kg per day; or from about 0.005 to about 300 mg/kg per day; or from about 0.01 to about 250 mg/kg per day, or from about 0.05 to about 100 mg/kg per day, or from about 0.5 to about 50 mg/kg per day. Within this range the dosage may be 0.0001 to 0.005, 0.005 to 0.05, 0.05 to 0.5, 0.5 to 5 or 5 to 50 mg/kg per day. For oral administration, the compositions may be provided in the form of tablets containing 0.01 to 1000 milligrams of the active ingredient, or 0.1 to 500, 1.0 to 400, or 2.0 to 300, or 3.0 to 200, particularly 0.01, 0.05, 0.1, 1, 4, 5, 10, 15, 20, 25, 30, 50, 75, 100, 125, 150, 175, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, or once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made by known procedures or as illustrated.

One of the principal routes used for preparation of compounds within the scope of the instant invention which bear a 1,1,3-trisubstituted cyclopentane framework 1-5 is depicted in Scheme 1. According to this route, keto acids 1-1 (preparation described in Schemes 2A, 2B, 2C, and 2D) is coupled to amines 1-2 (either commercially available or synthesized according to literature procedures). This can be accomplished in various ways, including by first converting the acid to its acid chloride with a reagent such as oxalyl chloride, and then combining with amine 1-2 in the presence of a base such as triethylamine. Reductive amination of 1-3 with an amine 1-4 (available commercially or synthesized according to literature procedures) using, for example, NaB(OAc)$_3$H or NaBH$_3$CN as the reducing agent gives chemokine receptor modulators 1-5. The compounds 1-5, which can be synthesized according to the chemistry described in Scheme 1 represent stereoisomeric mixtures (Eliel, E. E., Wilen, S. H., *Stereochemistry of Organic Compounds*, John Wiley & Sons, Inc., New York). In particular, compounds 1-5 are often obtained as a mixture of cis and trans isomers. When 1-1 is a single stereoisomer only 2 possible isomers of 1-5 can result (cis and trans); these can be separated by a variety of methods, including by preparative TLC, flash chromatography, MPLC, or by TPLC using a column with a chiral stationary phase. When 1-1 is racemic, a total of at least 4 possible isomers of 1-5 can be obtained. Again, these may be separated by BPLC using a column with a chiral stationary phase, or by a combination of the methods above.

SCHEME 1

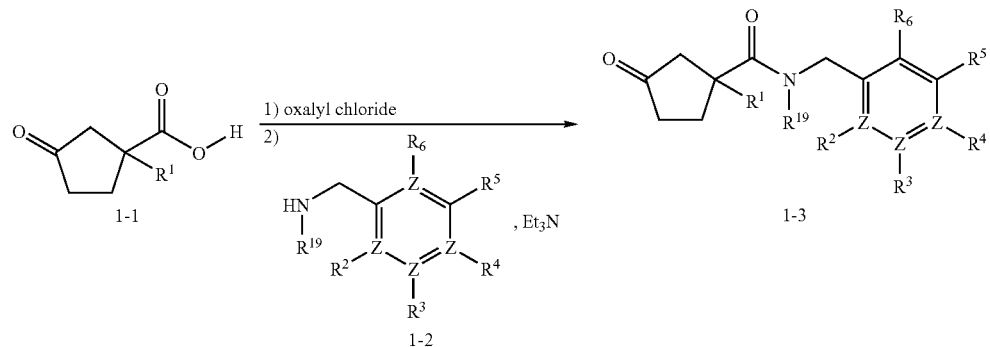

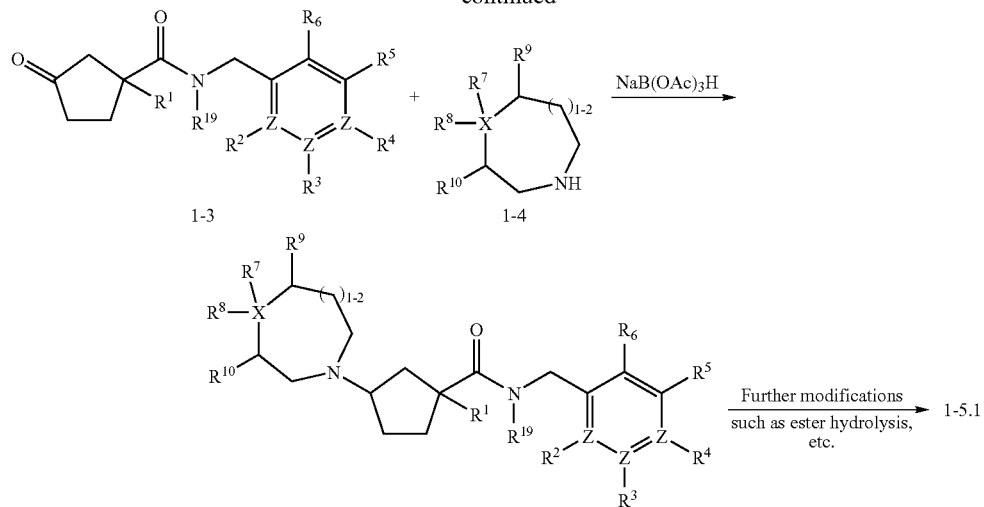

Furthermore, compounds 1-5 can themselves be modified to give new chemokine receptor modulators 1-5.1. For example, an ester functional group within a compound 1-5 can be hydrolyzed to the corresponding carboxylic acid, which also can be a chemokine receptor modulator.

As an alternate route to chemokine modulators 1-5 is shown in Scheme 1A. As depicted in this scheme, the ketoester 1-6 could be reductively aminated with amine 1-4 to form the amino ester 1-7 under a variety of conditions, including sodium triacetoxyborohydride or sodium cyanoborohydride. Alkylation of the ester 1-7 with an alkylating agent such as an alkyl chloride, bromide or iodide in the presence of an appropriate base such as lithium bis(trimethylsilyl)amide, affords the intermediate esters 1-8. These esters formed in the above mentioned transformations represent in general a mixture of 1,3-cis- and 1,3-trans-diastereoisomers, which could be separated into respective diastereoisomeric pairs using column chromatography. A similar diastereoisomeric separation could be also accomplished later, after the esters 1-8 were hydrolytically cleaved to yield the respective acids 1-9. This hydrolysis was readily accomplished under usual conditions, including lithium, sodium or potassium hydroxide, at ambient to elevated temperatures, depending on the nature of the ester group and substituent $R^1$. These diastereoisomers could be separated by crystallization from a variety of solvents, taking advantage of the finding, that the cis-diastereoisomeric acids are less soluble, when compared to their trans-epimers.

The compounds of formula 1-5a are then formed from the acids 1-9 and benzylamine derivatives 1-2 under standard amide-bond forming reaction conditions, including carbodiimide reagents, such as DCC, EDC and catalysts such as DMAP, HOAT or HOBT.

SCHEME 1A

Additionally, Intermediate 1-3 can also be resolved by Chiral HPLC to give 1-3a and 1-3b (Scheme 1B). This then would give cis/trans isomers 1-5a and 1-5b.

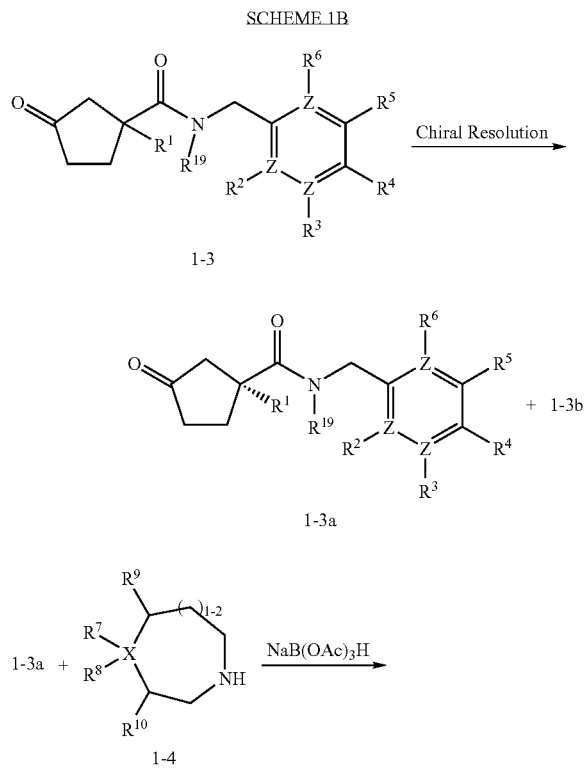

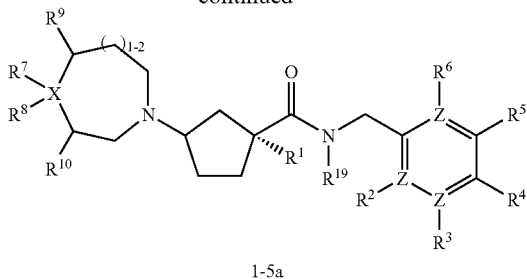

Another principal route for the synthesis of chemokine receptor modulators of the form 1-5a and 1-5c is depicted in Scheme IC. According to this route, intermediate 1-10 (described in Scheme 2C) is condensed with amine 1-2 using a peptide coupling reagent such as EDC to give 1-11.

The Boc protecting group is removed under standard conditions such as with HCl in a solvent such as dioxane followed by treatment of the resulting amine 1-12 with a dialdehyde 1-13 in the presence of a reducing agent such as sodium triacetoxyborohydride leads to a double reductive alkylation sequence with concomitant cyclization to give 1-5a.2. In accord with Scheme 1, further modifications, such as hydrolysis of an ester group present within 1-5a.2 can be effected to give new chemokine receptor modulators 1-5a.3. 1-12 can also be directly converted to chemokine modulators of the form 1-5c by direct reductive amination with ketone 1-14 (either commerically available or prepared according to literature procedures) in the presence of a reducing agent such as sodium triacetoxyborohydride or sodium cyanoborohydride. Further reductive amination with a ketone or aldehyde gives rise to new chemokine modulators 1-5c.1.

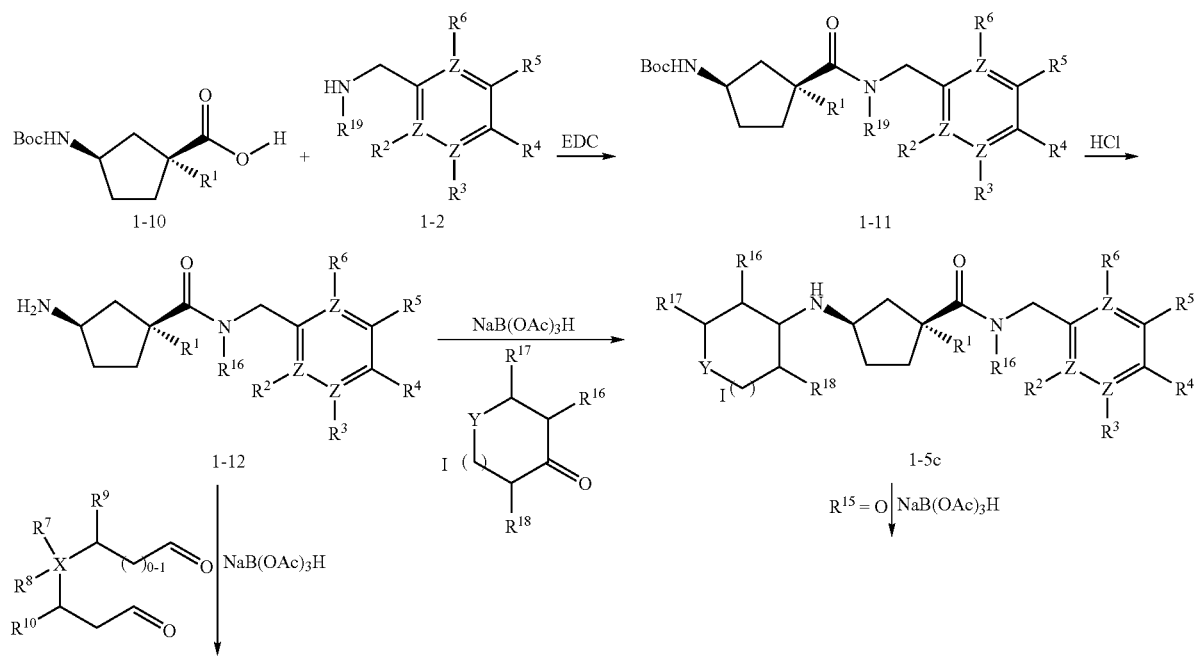

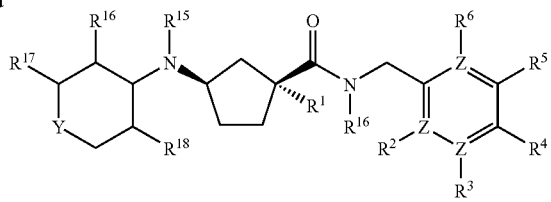

1-5c.1

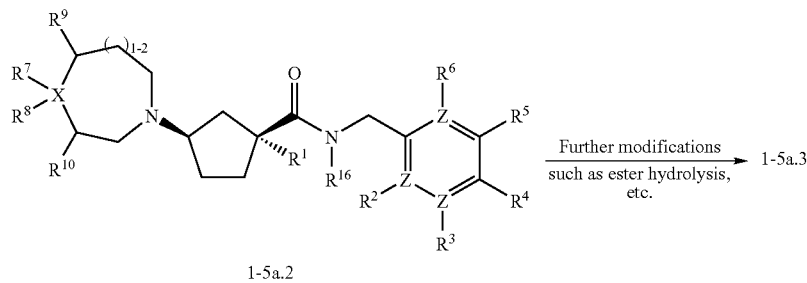

1-5a.2

One of the principal routes used for the preparation of Intermediate 1-1 and Intermediate 1-6 is outlined in Scheme 2A. According to this route, 3-oxocyclopentanecarboxylic acid (2-1), which can be synthesized following a known procedure (Stetter, H., Kuhlman, H., Liebigs Ann. Chim., 1979, 944) is esterified under standard conditions. When $R^{17}$ represents a tert-Butyl group, the respective ester 1-6 can be prepared by reacting the appropriate alcohol, in this case tert-butanol, with acid 2-1 in the presence of sulfuric acid. Protection of the oxo-group in 2-1 can be achieved by a number of ways (Greene, T., Wuts, P. G. M., Protective Groups in Organic Chemistry, John Wiley & Sons, Inc., New York, N.Y. 1991). The particularly suitable dimethyl acetal protecting group can be introduced using trimethyl orthoformate as a reagent in a suitable solvent such as dichloromethane and methyl alcohol in the presence of an acidic catalyst. Alternatively, in the case of $R^{30}$ being a methyl group, the acid 2-1 can be converted to 2-3 directly by using trimethyl orthoformate and an acidic catalyst, such as para-toluenesulfonic acid. An alkylation of esters 2-3 with an alkylating agent such as an alkyl chloride, bromide or iodide in the presence of an appropriate base such as lithium diisopropylamide, produces intermediates 2-4. The ester protecting group present in 2-4 can be removed in a number of ways, depending on the nature of the ester. Methyl esters ($R^{30}$=methyl) can be hydrolyzed in the presence of an acid or base at ambient or elevated temperatures, whereas tert-butyl esters ($R^{17}$=tert-butyl) can be easily cleaved under acidic conditions. Under these conditions, the dimethyl acetal is simultaneously deprotected to give 1-1.

SCHEME 2A

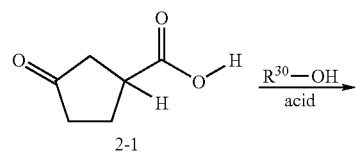

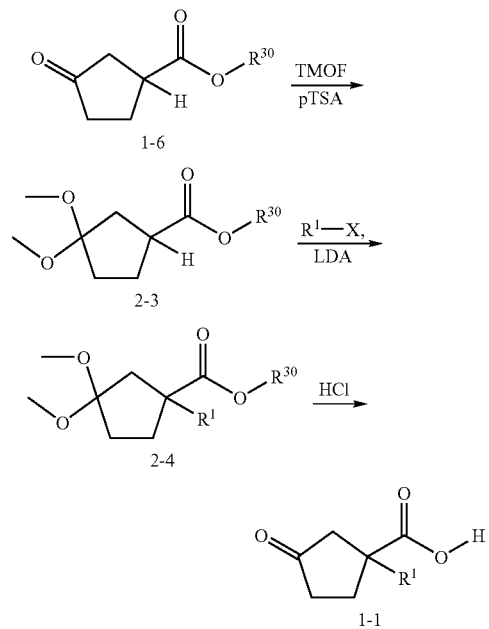

Intermediate 1-1 can also be prepared as a single stereoisomer (1-1a) in various ways including those depicted in Schemes 2B and 2C. According to Scheme 2B, racemic 1-1 can be converted to its benzyl ester. There are many ways to effect this esterification, one of which being by a sequence involving conversion to the corresponding acid chloride with, for example oxalyl chloride, followed by treatment with benzyl alcohol in the presence of a base such as triethylamine. Then the racemic benzyl ester 2-5 can be separated by chiral preparative BPLC to give 2-5a as a single stereoisomer. Removal of the benzyl group to give the chiral ketoacid 1-1a can be accomplished in several ways. One convenient way is by hydrogenolysis in the presence of a catalyst such as Pd/C.

SCHEME 2B

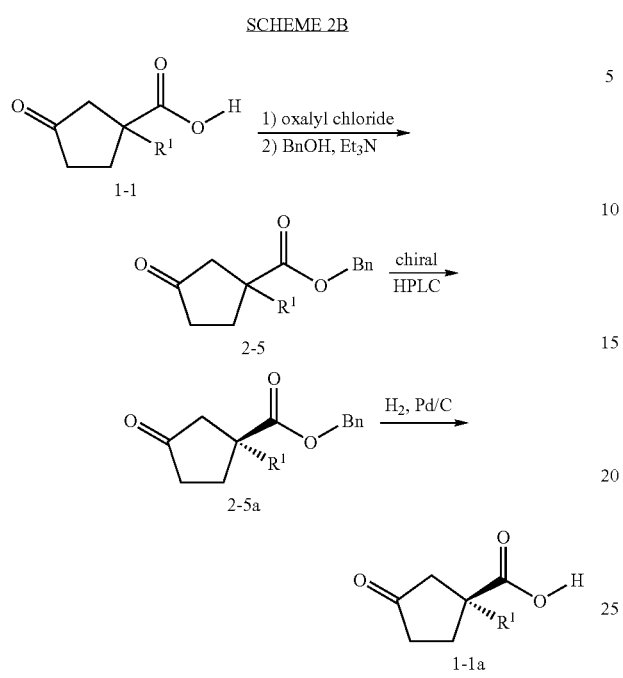

According to Scheme 2C, chiral ketoacid intermediate 1-1a and chiral amino acid 1-10 can be prepared starting from commercially available optically pure amino acid 2-6. Protection of the carboxylic acid group can be achieved in a variety of ways. When $R^{30}$ is methyl, esterification can be accomplished by treatment with methanol in the presence of an acid catalyst such as HCl. Treatment with Boc$_2$O results in protection of the amine group of 2-7. Stereoselective alkylation of ester 2-8 with an alkylating agent such as an alkyl chloride, bromide or iodide in the presence of an appropriate base such as lithium bis(trimethylsilyl)amide, produces intermediates 2-9. Hydrogenation in the presence of a catalyst such as Pd/C affords 2-10. Hydrolysis of the ester to give 2-11 can be achieved under standard conditions depending on the $R^{30}$ group. For example, when $R^{18}$ is methyl (methyl ester), hydrolysis can be accomplished by treatment with a base such as sodium hydroxide, lithium hydroxide, or potassium hydroxide, with or without heating. The Boc protecting group can be removed under standard acidic conditions, such as with HCl in a solvent such as dioxane, or with TFA. Oxidation of 2-12 to give 1-1a (as a single stereoisomer if constituent $R^1$ is achiral, or as a mixture of stereoisomers if constituent $R^1$ has a chiral center) can be achieved in several ways, including by treatment with NBS, followed by treatment with sodium methoxide.

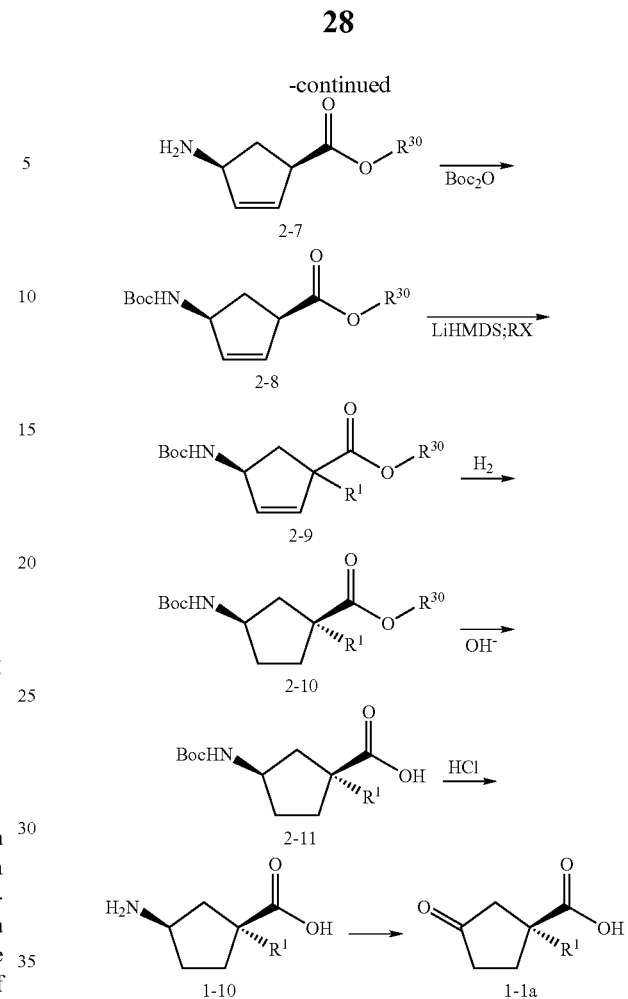

The enolate generated from ester 2-3 ($R^{30}$ being a benzyl or tert-Butyl group) in the presence of a strong base such as lithium diisopropylamide can be reacted with aldehydes ($R^{1a}$CHO) or ketones ($R^{1a}R^{2a}$CO) to produce the appropriate hydroxyalkyl substituted intermediates 2-4.1 as indicated in Scheme 2D. The resulting hydroxy group can be protected in various ways, including by treatment with acetic anhydride in the presence of a base such as triethylamine to give intermediates 2-4.2. Once again the ester protecting group is removed under conditions suitable for the particular protecting group. In the case of the tert-butyl esters ($R^{30}$ is t-butyl), deprotection is achieved under acidic conditions. The latter usually induces cleavage of the acetal protecting group as well, and the keto acids 1-1.1 can be prepared this way in an one-pot procedure. Their conversion to the final modulators of chemokine activity 1-9 can be achieved as described previously, with minor modifications to accommodate the protected hydroxy in 1-1.1.

SCHEME 2C

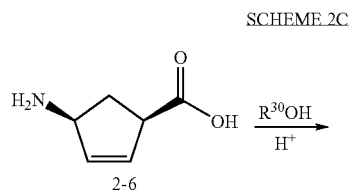

SCHEME 2D

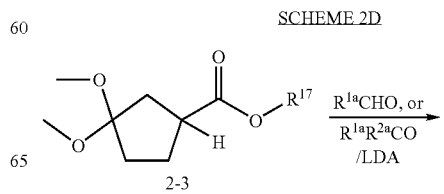

-continued

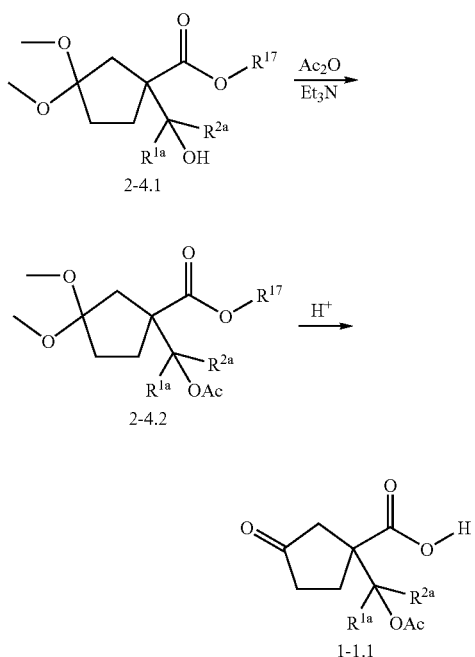

2-4.1

2-4.2

1-1.1

An alternate way of preparing acids 1-1 is shown in Scheme 2E. By this route, esters 2-12 are doubly alkylated using cis di-clorobutene as the elctrophile in the presence of a strong base such as lithium diisopropyl amide. The resulting olefins (2-13) can then be oxidized to the corresponding cyclopenatones 2-5, which upon hydrolysis give acids 1-1.

SCHEME 2E

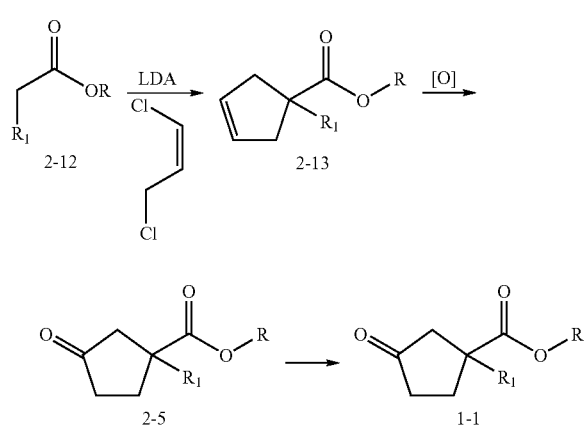

One way of preparing dialdehydes 1-13 is outlined in Scheme 3. According to this route, a (hetero)cycloalkene 3-1 is oxidatively cleaved with, for example, ozone followed by reduction with dimethylsulfide, to give the dialdehyde. Alternatively, in place of the dialdehydes 1-13 the intermediate ozonides 3-2 can themselves be used directly in the double reductive amination reaction leading to 1-5.2.

SCHEME 3

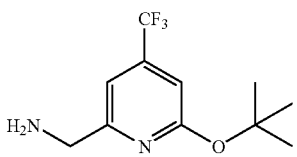

3-1

1-13

3-2

In some cases the order of carrying out the foregoing reaction schemes may be varied to facilitate the reaction or to avoid unwanted reaction products.

Intermediate 1

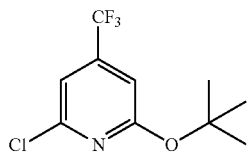

Step A

A solution of potassium tert-butoxide (13.16 g, 117.29 mmol) in anhydrous dimethyl formamide (60 mL) was cooled to 0° C. and a solution of 2,6-dichloro-4-trifluoromethyl pyridine (Lancaster, 12184) (16.89 g, 78.20 g) in dimethyl formamide (40 mL) was added drop-wise and the stirring was continued at 0° C. for 2 h. The reaction was quenched by pouring onto sat. solution of ammonium chloride (100 mL) and the crude product was extracted with hexane (3×100 mL). The combined organic phases were dried (anhydrous magnesium sulfate) and the solvent was evaporated to dryness. The product was further purified by gradient column chromatography on Silica-gel using ethyl acetate/hexane mixture as a eluent with gradually increasing concentration of ethyl acetate from 0 to 10% to yield 16.54 g (65.21 mmol, 84%). $^1$H NMR (500 MHz, CDCl$_3$): 7.04 (s, 1H), 6.80 (s, 1H), 1.62 (s, 9H).

Step B

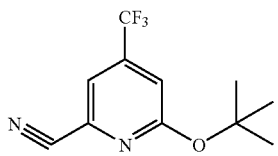

A mixture of the chloride from previous step (11.14 g, 44 mmol), zinc cyanide (10.33 g, 88 mmol) and tetrakis(triphenylphosphine)-palladium (0) (3.90 g, 3.52 mmol) in dry dimethyl formamide (50 mL) were thoroughly degassed by nitrogen/vacuum cycling and stirred at 95° C. overnight. The reaction was quenched by pouring into 200 mL of water and the product was extracted into hexane. The organic layer was filtered through a plug of Celite and evaporated to dryness to yield 12.10 g of crude product containing triphenylphosphine as the main contaminant. This residue was dissolved in tetrahydrofurane (50 mL). a solution of hydrogen peroxide in water (10 mL, 30%) was added and this mixture was stirred at room temperature for 30 minutes. The solvent was evaporated to dryness and the product was separated from triphenylphosphine oxide by column chromatography as described in Step A (ethyl acetate in hexanes, 0 to 5%). According to this procedure 4.59 g (18.79 mmol, 43%) of pure product was obtained. $^1$H NMR (500 MHz, CDCl$_3$): 7.40 (s, 1H), 7.09 (s, 1H), 1.63 (s, 9H).

Step C

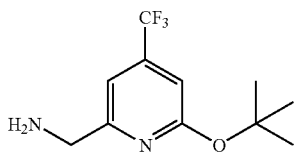

A solution of the nitrile from Step B (4.39 g, 18 mmol) and Raney Nickel (27 g) in a mixture of ethyl alcohol (160 mL) and aqueous ammonium hydroxide (40 mL) was hydrogenated in a Parr shaker at 50 psi pressure for 4 hrs. The catalyst was filtered off and the solvent was removed on a rotary evaporator. The obtained crude product (4.01 g) was used without further purification.

Intermediate 2

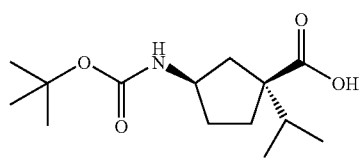

Procedure A:

Step A

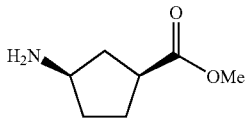

A mixture of (1S)-(+)-2-azabicyclo[2.2.1]hept-5-en-3-one (10.3 g, 94.4 mmol) in ethyl acetate (200 mL) and 10% Pd/C (0.5 g), was hydrogenated at room temperature. After 24 h the reaction mixture was filtered and evaporated leaving behind 10.4 g (100%) of the product that was taken in 250 mL methanol and HCl (12 M, 6 mL). The resultant mixture was stirred at room temperature, until the reaction was complete (72 h). Evaporation of methanol followed by drying under high vacuum, yielded title compound as an off white solid (16.0 g, 96%). $^1$H NMR (500 MHz, D$_2$O): δ 3.70 (s, 3H), 3.01 (m, 1H), 2.38 (m, 1H), 2.16-1.73 (m, 6H).

Step B

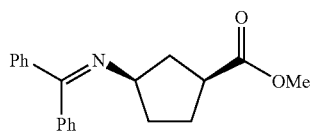

To a suspension of the intermediate from Step A (10.2 g, 56.8 mmol) in dry dichloromethane (200 mL) was added benzophenone imine (10.2 g, 56.8 mmol) at room temperature and the resultant mixture was stirred for 24 h. The reaction mixture was filtered and the filtrate was evaporated, to leave behind a yellow oil that was triturated with ether (100 mL), filtered and evaporated. This operation was repeated twice to ensure that the product was free of ammonium chloride impurities. The resultant oil was thoroughly dried under vacuum to yield the title compound (18.03 g, >100%) and required no further purification. 1H NMR (500 MHz, CDCl3): δ 7.5-7.18 (m, 10H), 3.75 (m, 1H), 3.7 (s, 3H), 2.78 (m, 1H), 2.26-1.71 (m, 6H).

Step C

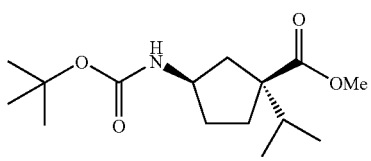

To a solution of lithium diisopropylamide (prepared from diisopropylamine (7.7 g, 76 mmol) and n-butyllithium (30.4 mL, 2.5 M in hexanes, 76 mmol) in tetrahydrofuran (120 mL) at −78° C. was added the ester from step B (18.0 g, 58.6 mmol). The resultant burgundy colored solution was stirred for 20 min after which it was quenched with 2-iodopropane (14.9 gm, 88 mmol). The reaction mixture was gradually warmed over 3 h to 0° C. and this temperature was maintained for an additional 3 h. Reaction was quenched with water and extracted with ethyl acetate. The organic layer was washed with water, brine, dried (anhydrous magnesium sulfate) and concentrated to yield an oil. To the solution of the crude Schiff base (20.0 g) in tetrahydrofuran (100 mL) was added HCl (5.0 mL, 12 M). The resulting reaction mixture was allowed to stir at room temperature for 3 h. After the removal of all volatiles, the hydrochloride salt was taken up into dichloromethane (250 mL), saturated solution of sodium bicarbonate (250 mL) and di-tert-butyl dicarbonate (26.0 g, 1.4 Eq.) were added. The resultant mixture was vigorously stirred overnight at room temperature. The organic layer was separated and washed with water, brine, dried (anhydrous magnesium sulfate) and concentrated to yield an oil. Purification by flash column chromatography (eluent: hexanes/ethyl acetate 19:1) gave the desired product (4.91 g, 30%). 1H NMR (500 MHz, CDCl3): 4.79 (br, 1H), 4.01 (m, 1H), 3.71 (s, 3H), 2.18-1.60 (m, 6H), 1.44 (s, 9H), 0.87 (d, J=6.9 Hz, 3H), 0.86 (d, J=6.9 Hz, 3H).

Step D

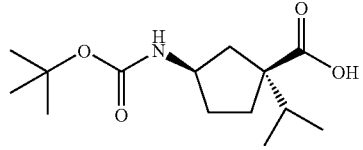

To a solution of the ester from Step C (4.91 g, 17.2 mmol) in methanol (100 mL) was added a solution of LiOH (3.6 g, 85 mmol) in water (20 mL) and tetrahydrofuran (10 mL). The resultant mixture was heated at 80° C. until the reaction was complete (18 h). The methanol was removed in vacuo and the crude product was taken up with water/ethyl acetate (200 mL, 1:4) and cooled to 0° C. The acidity of the mixture was adjusted to pH 6. The ethyl acetate layer was separated, washed with water, brine, dried (anhydrous magnesium sulfate) and concentrated to yield an oil. Purification by flash column chromatography (eluent: hexanes/ethyl acetate 1:1+ 2% AcOH) gave Intermediate 11 (3.9 g, 84%). 1H NMR (500 MHz, CDCl3): 11.36 (br, 1H), 6.49 (br, 1H), 4.83 (m, 1H), 3.71 (s, 3H), 2.30-1.55 (m, 6H), 1.46 (s, 9H), 0.94 (d, J=6.9 Hz, 3H), 0.933 (d, J=6.9 Hz, 3H).

Procedure B:

Step A:

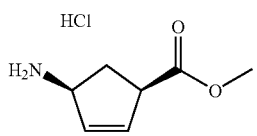

Commercially available (1R,4S)-4-aminocyclopent-2-ene-1-carboxylic acid was converted to its methyl ester hydrochloride salt via classical procedures.

Step B:

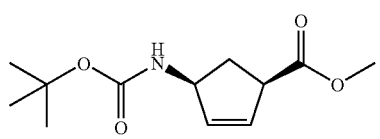

To a suspension of amine from Step A (6.31 g, 35.5 mmol) in acetone (40 mL) and water (20 mL) was added solid NaHCO$_3$ (6.6 g, 78 mmol) in portions. After 5 min, a solution of di-tert-butyl dicarbonate (8.5 g, 39 mmol) in acetone (60 mL) was added and the reaction mixture was stirred at room temperature. After 3 h, acetone was removed in vacuo and the residue was partitioned between ether (500 mL) and saturated aqueous NaHCO$_3$ solution (120 mL). The ether layer was further washed with aqueous NaHCO$_3$ solution (1×100 mL), brine (1×100 mL), dried over anhydrous Na$_2$SO$_4$, concentrated and purified by flash chromatography (15% ethyl acetate/hexanes) to afford the product (7.25 g, 85%).

Step C:

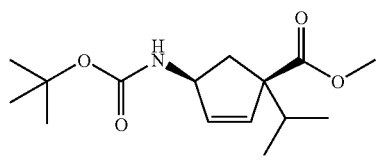

To a solution of lithium bis(trimethylsilyl)amide (10.4 g, 62.1 mmol) in tetrahydrofuran (100 mL) was added a solution of the intermediate from Step B (6.71 g, 27.8 mmol) in tetrahydrofuran (10 mL) over 10 min at −78° C. The resulted solution was stirred at −78° C. for 30 min before isopropyl iodide (3.3 mL, 33 mmol) was added in one portion. The reaction was allowed to warm up to −25° C. and this temperature was maintained overnight. The reaction was then quenched with an aqueous saturated NH$_4$Cl solution (250 mL). The organic layer was separated and the aqueous layer was further extracted with diethyl ether (3×100 mL). The combined organic layers were then washed with brine (1×100 mL), dried over anhydrous Na$_2$SO$_4$, filtered, concentrated and purified by flash chromatography (5-10% ethyl acetate/hexanes) to give the product (5.66 g, 72%) as a clear oil (cis/trans=4.3/1). $^1$H NMR (500 MHz, CDCl$_3$) cis-isomer: δ 5.79 (s, 2H), 4.75 (m, 1H), 3.72 (s, 3H), 2.28-2.20 (m, 2H), 2.0 (dd, J=15, 4 Hz, 1H), 1.45 (s, 9H), 0.85 (d, J=6.6 Hz, 3H), 0.81 (d, J=7 Hz, 3H).

Step D:

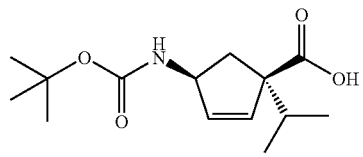

To a solution of the product from step C (1.6 g, 5.7 mmol) in tetrahydrofuran (50 mL), methanol (50 mL) and water (10 mL) was added LiOH monohydrate (400 mg) and the reaction was heated to reflux overnight until the TLC indicated that the reaction was complete. The organic solvents were removed in vacuo and the aqueous layer was washed with ether (1×) and then acidified slowly with concentrated HCl until the pH reached 4. The resulting suspension was extracted with CH$_2$Cl$_2$ (3×). The combined organic layers were dried over anhydrous MgSO$_4$, filtered and concentrated to give the product as a mixture of two cis/trans isomers (1.5 g) as a foaming yellow solid. This solid was dissolved in ethyl acetate (2 mL) with heating and diluted with hexanes (50 mL) to give a clear solution. This solution was allowed to cool to room temperate slowly over 1 h and then maintained at −25° C. in a freezer overnight. The trans-isomer was crystalized out along with some of the desired cis-isomer (500 mg total). The mother solution was collected and concentrated to give the title compound (1 g, 66%, cis-isomer only). $^1$H NMR (500 MHz, CDCl$_3$) cis-isomer: δ 5.80 (m, 2H), 4.80 (m, 1H), 2.40-2.20 (m, 2H), 2.15-2.0 (m, 1H), 1.5 (m, 9H), 1.0-0.8 (m, 3H).

Step E:

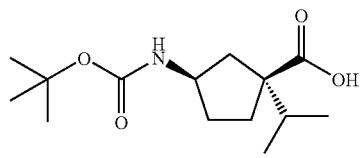

To a solution of the product from Step D (1 g) in ethanol (30 mL) was added 10% Pd/C (100 mg) and the resulting mixture was agitated on a Parr apparatus at 50 lb pressure of H2 overnight. The mixture was filtered through celite and concentrated in vacuo to afford the title compound (1 g, 99%). 1H NMR (500 MHz, CDCl3): 11.36 (br, 1H), 6.49 (br, 1H), 4.83 (m, 1H), 3.71 (s, 3H), 2.30-1.55 (m, 6H), 1.46 (s, 9H), 0.94 (d, J3=6.9 Hz, 3H), 0.933 (d, 3=6.9 Hz, 3M).

Intermediate 3

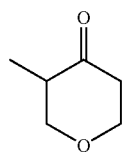

Intermediate 1 was prepared according to the procedure described in *J. Am. Chem. Soc.,* 1991, 113, 2079-2089.

Intermediate 4

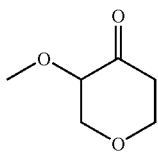

Step A

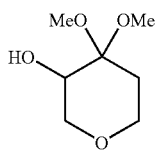

To a mixture of 5,6-dihydro-4-methoxy-2H-pyran (10.0 g, 87.5 mmol) in methanol (200 mL) at 0° C. was added dropwise a solution of 3-chloroperoxy-benzoic acid (30.2 g, 175 mmol) in methanol (50 mL) via an addition funnel. The resulting solution was stirred for 5 h allowing it to warm to room temperature. The methanol was removed under reduced pressure affording a white solid. The material was dissolved in 500 mL of dichloromethane and cooled to 0° C. To the mixture, while stirring vigorously, was added in portions an excess of solid calcium hydroxide (50-60 g). After stirring an additional 30 min, the mixture was filtered through a plug of celite and the filtrate was evaporated under reduced pressure to afford 11.62 g (82%) of the desired product as a clear oil. $^1$H NMR (500 MHz, CDCl$_3$) δ 3.88-3.80 (m, 2H), 3.73-3.68 (m, 2H), 3.54-3.48 (m, 1H), 3.28 (s, 3H), 3.27 (s, 3H), 2.00-1.93 (m, 1H), 1.82-1.77 (m, 1H).

Step B

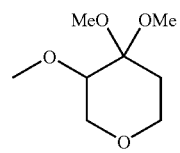

To a cooled (0° C.) solution of the product from Step A, Intermediate 3 (9.40 g, 58.0 mmol) in tetrahydrofuran (200 mL), under nitrogen, was slowly added NaH (2.32 g, 58.0 mmol) and the resulting slurry was stirred for 1 h at 0° C. Iodomethane (7.22 mL, 116 mmol) was then added via syringe to the slurry and the resulting mixture was stirred overnight allowing it to warm to room temperature. The reaction was quenched with a saturated solution of ammonium chloride (200 mL) and the organic layer was then removed using a separatory funnel. The aqueous layer was extracted with ether (3×150 mL) and all the organics were combined, dried over anhydrous sodium sulfate, filtered, and evaporated in vacuo. Purification was accomplished by flash column using a stepwise gradient eluant of 10-60% ether/hexanes to afford 8.46 g (83%) of the desired product as a clear oil. $^1$H NMR (500 MHz, CDCl$_3$) δ 3.98 (dd, J=2.5, 12.4 Hz, 1H), 3.77 (ddd, J=3.5, 7.1, 10.8 Hz, 1H), 3.57 (dd, J=1.4, 12.4 Hz, 1H), 3.50 (dd, J=2.5, 11.7 Hz, 1H), 3.46 (s, 3H), 3.25 (s, 3H), 3.22 (s, 3H), 3.22-3.20 (m, 1H), 1.96 (ddd, J=4.7, 11.8, 16.5 Hz, 1H), 1.75 (br dd, J=1.7, 14.2 Hz, 1H).

Step C

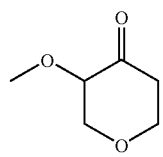

A solution of the product from Step B, Intermediate 3 (3.0 g, 17.04 mmol) in tetrahydrofuran/water (60 mL/10 mL) was treated with concentrated hydrochloric acid (6 mL) and the resulting solution was stirred at room temperature for 1 h. The mixture was concentrated in vacuo to remove the tetrahydrofuran and the aqueous layer then extracted with ether (6×50 mL). The organics were combined, dried over anhydrous sodium sulfate, filtered, and evaporated under reduced pressure to afford intermediate 24 (1.75 g, 79%) as a clear oil. $^1$H NMR (500 MHz, CDCl$_3$) δ 4.23 (ddd, J=1.2, 11.4, 12.4 Hz, 1H), 4.15-4.09 (m, 1H), 3.82 (dd, J=5.95, 8.7 Hz, 1H), 3.74 (ddd, J=5.5, 8.5, 13.6 Hz, 1H), 3.56 (dd, J=8.8, 11.3 Hz, 1H), 3.50 (s, 3H), 2.61 (app dd, J=5.0, 8.9 Hz, 2H).

Intermediate 5

Step A

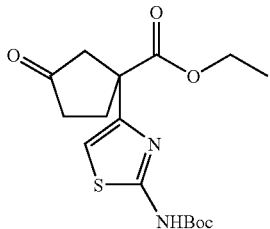

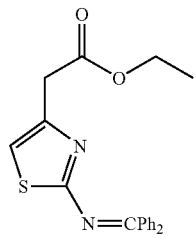

A neat mixture of 54 g (0.29 mole) ethyl (2-aminothiazol-4-yl)acetate and 50 g (0.276 mole) benzophenone imine was stirred at 190° C. for 5 h and then cooled at RT and diluted with 100 mL of CH2Cl2. The entire mixture was transferred onto a silica gel column and eluted with 20% EtOAc/Hexane. The title compound was obtained as light-yellow solid (70 g, 69% yield). $^1$H NMR (300 MHz, CDCl$_3$): δ 1.26 (t, 3H), 3.74 (s, 2H), 4.15 (q, 2H), 6.87 (s, 1H), 77.25-7.86 (m, 10H); Mass Spectrum (NH$_3$-CI): m/z 351 (M+1).

Step B

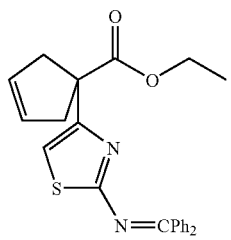

To a mixture of 35 g (0.10 Mole) of the Schiff base ester (Step A above), cis-1,3-dichloro-2-butene (13 mL, 0.11 Mole) in 500 mL of DME at RT was added in multiple portions solid NaH (60% oil, 10.0 g, 0.25 Mole). The resulting mixture was stirred for 2 days, poured into 2000 mL of ice-water, extracted with 1500 mL of ether. The ether layer was washed with water (3×500 mL), dried over Na2SO4 and evaporated. FC (Silica Gel, 5% EtOAc/Hexane) afforded the title compound as an oil (24 g, 59%). $^1$H NMR (300 MHz, CDCl$_3$): δ 1.20 (t, 3H), 2.87 (d, 2H), 3.19 (d, 2H), 4.14 (q, 2H), 5.29 (s, 2H), 6.71 (s, 1H), 7.26-7.81 (m, 10H). Mass Spectrum (NH$_3$-CI): m/z 403 (M+1).

Step C

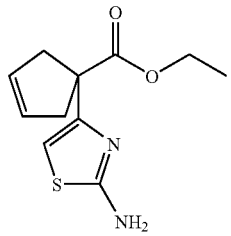

24.0 g (0.059 Mol) of the cyclopentene Schiff base (Step B above) was dissolved in 100 mL of 4N HCl/dioxane. After 1 h, 1.8 mL of water was added. The mixture was stirred for 3 h, evaporated to dryness. The residue was dissolved in 100 mL of CH2Cl2 and added 15 mL of DIEA. The entire mixture was dumped onto a silica gel column, eluted with 20% EtOAc/Hexane to remove benzophenone, then eluted with 40% EtOAc/Hexane to give the title compound as a light yellow solid (12.0 g, 85%). $^1$H NMR (300 MHz, CDCl$_3$): δ 1.19 (t, 3H), 2.79 (d, 12H), 3.15 (d, 2H), 4.13 (q, 2H), 5.66 (s, 2H), 5.82 (wide, 2H), 6.19 (s, 1H).

Step D

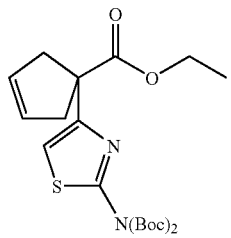

A mixture of 12 g (0.05 Mol) of the aminothiazole (Step C above), 28 g (0.13 Mol) of di-tert-butyl dicarbonate and 0.6 g of DMAP in 250 mL of CH2Cl2 was stirred overnight, and evaporated. The title compound (21.0 g, 96%) was obtained as a yellow oil after FC purification on silica gel (10% EtOAc/Hexane). $^1$H NMR (300 MHz, CDCl$_3$): δ 1.18 (t, 3H), 1.49 (d, 18H), 2.88 (d, 2H), 3.18 (d, 2H), 4.13 (q, 2H), 5.65 (s, 2H), 6.83 (s, 1H). Mass Spectrum (NH$_3$-CI):m/z 439 (M+1).

Step E

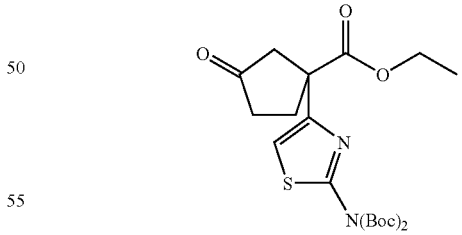

To a solution of 13.1 g (0.03 Mol) of the ester (Step D above) in 50 mL of anhydrous ether at −78° C. was added dropwise a solution of BH3.DMS in THF (14 mL, 0.024 mmol). The cooling bath was removed and the mixture was stirred at RT for 3 h, diluted with 250 mL of CH2Cl2, added 25 g of sodium acetate and 55 g of PCC. The mixture was stirred overnight. The entire mixture was dumped onto a silica gel column and eluted with in 10% EtOAc/Hexane and then 30% EtOAc/Hexane. Two components were obtained. The fast-eluted isomer (yellow oil, 6.0 g) was identified as the title compound.

¹H NMR (300 MHz, CDCl₃): δ 1.21 (t, 3H), 1.50 (s, 18H), 2.33 (t, 2H), 2.42-2.70 (m, 2H), 2.78-3.10 (dd, 2H), 4.18 (q, 3H), 6.88 (s, 1H). Mass Spectrum (NH₃-CI): m/z 455 (M+1).

Step F

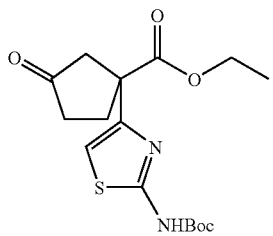

The slow-eluted component from FC in the synthesis of the cyclopentene (Step E above) was proved to be the title compound (gummy material, 1.80 g). ¹H NMR (300 MHz, CDCl₃): δ 1.11. (t, 3H), 1.46 (s, 9H), 2.27 (3, 2H), 2.38-2.62 (m, 2H), 2.64-3.00 (dd, 2H), 4.11 (q, 2H), 6.66 (s, 1H). Mass Spectrum (NH₃-CI): m/z 355 (M+1).

Intermediate 6

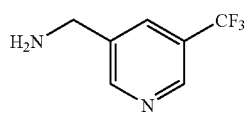

Step A

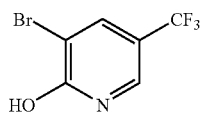

To a solution of 5-trifluoromethyl-2-pyridinol (21.37 g, 131 mmol), and sodium acetate (11.23 g, 107 mmol) in glacial acetic acid was added bromine (6.94 ml, 135 mmol), and the resulting mixture stirred at 80° C. for 2 hours. The cooled reaction mixture was evaporated and the residue basified by the addition of saturated NaHCO₃ (500 ml), and extracted with ethyl acetate (3×300 ml); the combined ethyl acetate layers were dried over MgSO₄, filtered and evaporated in vacuo to give the product (30.21 g, 95%); ¹H NMR 500 MHz (CDCl₃) δ=8.00 (1H, d, J=2.29 Hz), 8.16 (1H, d, J=2.29 Hz).

Step B

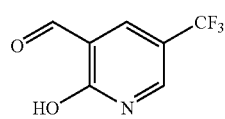

To a suspension of sodium hydride (5.5 g of a 60% dispersion in oil, 137 mmol) in anhydrous tetrahydrofuran (500 ml) under an atmosphere of nitrogen was added in a portionwise manner the product from step A (30 g, 124 mmol). After hydrogen evolution had ceased the mixture was cooled to −78° C. and tert-butyl lithium (161 ml of a 1.7M solution in pentane, 274 mmol) was added at such a rate that the temperature did not rise above −65° C. The mixture was stirred for 5 mins then N,N-dimethylformamide (30 ml, 388 mmol) added keeping the temperature below −50° C. The mixture was allowed to warm to room temperature and partitioned between ethyl acetate (500 ml) and 2N HCl (500 ml); the organic layer was seperated, washed with saturated NaCl, dried over MgSO₄, filtered and evaporated in vacuo. The residue was triturated with a mixture of 10% Et₂O in hexanes, the solid removed by filtration and air dried to give the product (18.9 g, 80%); ¹H NMR 500 MHz (d⁶-DMSO) □=8.05 (1H, d, J=2.74 Hz), 8.35 (1H, d, J=1.60 Hz), 10.03 (1H, s).

Step C

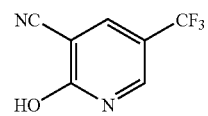

A mixture of the product from step B (18.9 g, 99 mmol), sodium formate (7.4 g, 109 mmol), and hydroxylamine hydrochloride (7.56 g, 109 mmol) in formic acid (225 ml) was stirred at room temperature for 2 hours and then heated at reflux for 20 hours. The cooled reaction mixture was left standing at room temperature for 72 hours, then poured into water (750 ml) and extracted with ethyl acetate (3×200 ml). The combined ethyl acetate layers were washed with water (2×500 ml), saturated NaHCO₃ (250 ml), saturated NaCl (150 ml), dried over MgSO₄, filtered and evaporated in vacuo to give the product (7 g, 37%); ¹H NMR 500 MHz (d⁶-DMSO) □=8.32 (1H, d, J=1.61 Hz), 8.45 (1H, d, J=2.74 Hz).

Step D

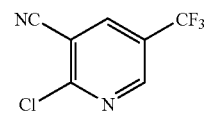

To phosphorous oxychloride (3.82 ml, 41 mmol) was added quinoline (2.5 ml, 21 mmol), followed by the product from step C, and the resulting mixture heated at 120° C. for 2 hours. The mixture was cooled to 100° C. and water (20 ml) cautiously added. The mixture was cooled to room temperature and basified by the addition of saturated NaHCO₃ (200 ml), and extracted with ethyl acetate (3×150 ml). The combined ethyl acetate layers were dried over MgSO₄, filtered and concentrated in vacuo. The residue was purified by column chromatography on silica elution with 30% ethyl acetate in hexanes to give the product (5.7 g, 75%); ¹H NMR 500 MHz (CDCl₃) □=8.27 (1H, s), 8.88 (1H, s).

Step E

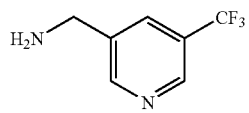

To a solution of the product from step D (1 g, 4.9 mmol), in a mixture of ethyl alcohol (40 ml) and ammonium hydroxide (5 ml) was added Raney nickel (300 mg), and the resulting mixture hydrogenated at 40 psi for 7 hours. The catalyst was removed by filtration and the filtrate concentrated in vacuo. The residue was purified by MPLC (Biotage Flash 40) elution with 2% CH$_3$OH in CH$_2$Cl$_2$ containing 0.5% NH$_4$OH to give the product (250 mg, 30%); $^1$H NMR 500 MHz (CDCl$_3$) □=4.00 (2H, s), 7.95 (1H, s), 8.75 (2H, d, J=5.26 Hz).

EXAMPLE 1

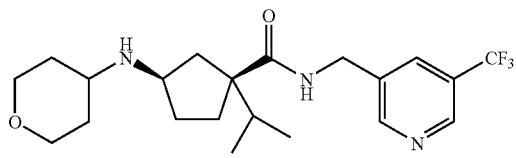

Step A

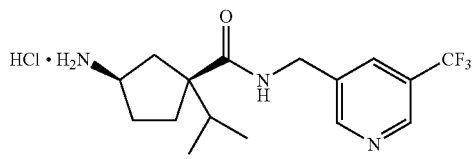

To a solution of Intermediate 2 (500 mg, 1.84 mmol) in methylene chloride (25 mL) was added Intermediate 6 (358, 2.03 mmol), N,N-diisopropylethylamine (1.06 mL, 6.08 mmol), 1-hydroxy-7-azabenzotriazole (276 mg, 2.03 mmol) and EDC (583 mg, 3.04 mmol), and the solution stirred overnight. The mixture was extracted with methylene chloride, washed with water, dried under sodium sulfate and concentrated in vacuo. The crude product was purified through MPLC (0-60% ethyl acetate/hexanes). 4 N hydrochloric acid was added, and solution was concentrated iin vacuo to yield the desired product (660 mg, 90%).

Step B

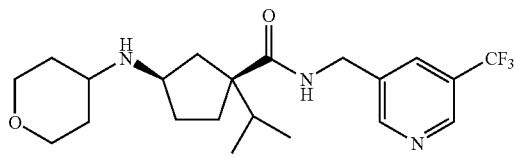

To a solution of the product from Step A (168 mg, 0.42 mmol) in methylene chloride (20 mL) was added tetrahydro-4H-pyran-4-one (50 mg, 0.50 mmol) and N,N-diisopropylethylamine (260 uL, 1.5 mmol). After adding molecular sieves (25 mg), sodium triacetoxyborohydride (1.06 g, 5.00 mmol) was added and mixture stirred overnight. The mixture was extracted with methylene chloride, washed with sodium bicarbonate, dried under sodium sulfate and concentrated iiz vacuo. The crude product was purified on preparation plates (10/89/1, methanol/methylene chloride/ammonium hydroxide), 4 N hydrochloric acid was added and the solution was concentrated in vacuo to yield Example 1 (50 mg, 30%). LC-MS: MW calculated 413.23, found 414.5.

EXAMPLE 2

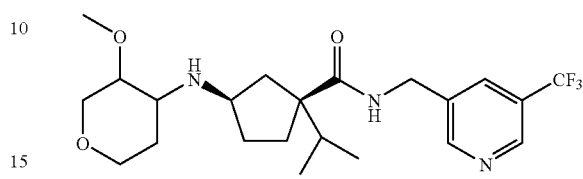

Step A

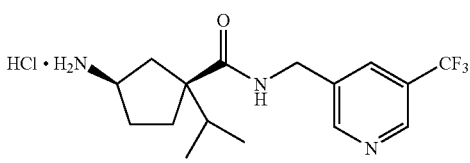

To a solution of Intermediate 2 (500 mg, 1.84 mmol) in methylene chloride (25 mL) was added Intermediate 6 (358, 2.03 mmol), N,N-diisopropylethylamine (1.06 mL, 6.08 mmol), 1-hydroxy-7-azabenzotriazole (276 mg, 2.03 mmol) and EDC (583 mg, 3.04 mmol), and the solution stirred overnight. The mixture was extracted with methylene chloride, washed with water, dried under sodium sulfate and concentrated in vacuo. The crude product was purified through MPLC (0-60% ethyl acetate/hexanes). 4 N hydrochloric acid was added, and the solution was concentrated in vacuo to yield the desired product (660 mg, 90%).

Step B

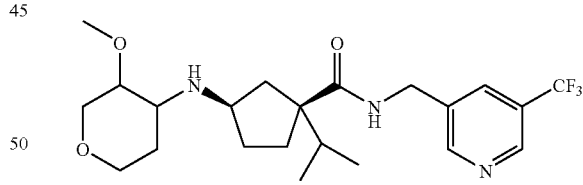

To a solution of the product from Step A (50 mg, 0.39 mmol) in methylene chloride (15 mL) was added Intermediate 4 (128 mg, 0.32 mmol) and N,N-diisopropylethylamine (203 uL, 1.17 mmol). After adding molecular sieves (15 mg), sodium triacetoxyborohydride (827 mg, 3.9 mmol) was added and mixture stirred overnight. The mixture was extracted with methylene chloride, washed with sodium bicarbonate, dried under sodium sulfate and concentrated in vacuo. The crude product was purified on preparation plates (10/89/1, methanol/methylene chloride/ammonium hydroxide). 4 N hydrochloric acid was added and the solution was concentrated in vacuo to yield Example 2 (40 mg, 28%). LC-MS: MW calculated 443.24, found 444.5.

EXAMPLE 3

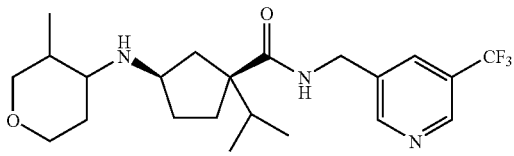

Step A

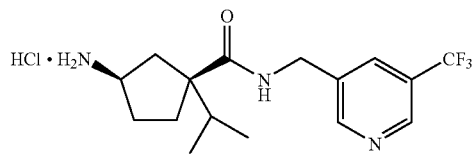

To a solution of Intermediate 2 (500 mg, 1.84 mmol) in methylene chloride (25 mL) was added Intermediate 6 (358, 2.03 mmol), N,N-diisopropylethylamine (1.06 mL, 6.08 mmol), 1-hydroxy-7-azabenzotriazole (276 mg, 2.03 mmol) and EDC (583 mg, 3.04 mmol), and the solution stirred overnight. The mixture was extracted with methylene chloride, washed with water, dried under sodium sulfate and concentrated in vacuo. The crude product was purified through MPLC (0-60% ethyl acetate/hexanes). 4 N hydrochloric acid was added, and the solution was concentrated in vacuo to yield the desired product (660 mg, 90%).

Step B

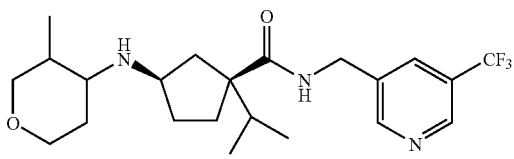

To a solution of Intermeidiate 3 (17 mg, 0.150 mmol) in methylene chloride anhydr. (15 mL) was added the product of Step A (50 mg, 0.125 mmol) and N,N-diisopropylethylamine (65 uL, 0.375 mmol). After adding molecular sieves (10 mg), sodium triacetoxyborohydride (185 mg, 0.875 mmol) was added and mixture stirred overnight. The mixture was extracted with methylene chloride, washed with sodium bicarbonate, dried under sodium sulfate and concentrated in vacuo. The crude product was purified on preparation plates (8/91.2/0.8, methanol/methylene chloride/ammonium hydroxide and run on an OD Chiral Column (97/3, hexanes/ethyl acetate) to separate all isomers. 4N hydrochloric acid was added and the isomers were concentrated in vacuo to give the desired product (70 mg, 79%). LC-MS: MW calculated 427.24, found 428.5.

EXAMPLE 4

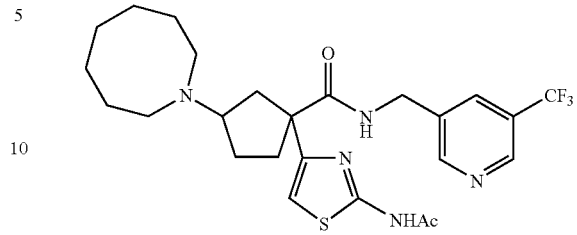

Step A

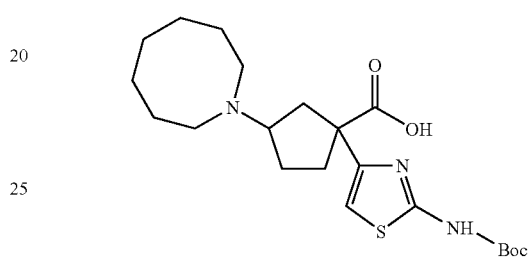

To a solution of Intermediate 5 (2.20 g, 4.83 mmol) in THF (25 mL) was added heptamethyleneimine (610 µL, 4.83 mmol) followed by NaBH(OAc)$_3$ (3.30 g, 15.6 mmol). The reaction was stirred at room temperature overnight. Methanol (5 mL) and water (1 mL) was then added to give a clear solution. LiOH (1.00 g) was then added. After stirred at room temperature for another 16 hours, the reaction was acidified by the addition of AcOH (3 mL). ¼ of this mixture was purified on reverse phase HPLC to give 300 mg of the desired acid as a mixture of cis/trans isomers (59% yield based on the crude materials used in the purification). LC-MS for $C_{21}H_{34}N_3O_4S$ [M+H$^+$]: calculated 424.22, found 424.25.

Step B

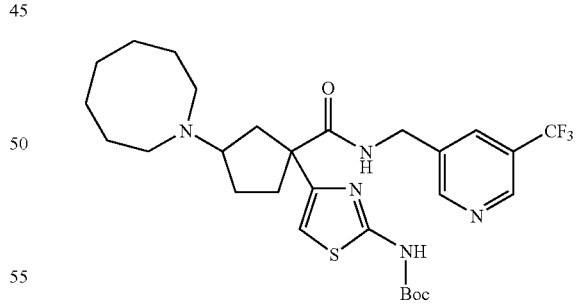

To a solution of the acid from step A (80 mg, 0.19 mmol), 3-(aminomethyl)-5-(trifluoromethyl)pyridine (58 mg, 0.233 mmol), DMAP (5.0 mg) and DIEA (70 µL, 0.402 mmol) in CH$_2$Cl$_2$ (2 mL) was added EDC (56 mg, 0.294 mmol). The reaction was stirred at room temperature for 10 hours before concentrated and purified by reverse-phase HPLC to give the desired product (60 mg, 54%) as a mixture of cis/trans isomers. LC-MS for $C_{28}H_{39}F_3N_5O_3S$ [M+H$^+$]: calculated 582.26, found 582.35.

Step C

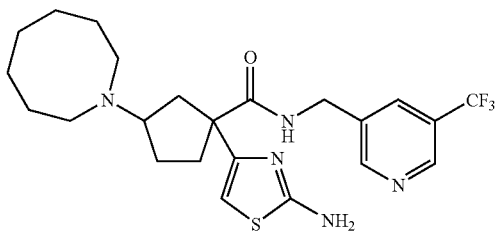

The product of step B (60 mg, 0.103 mmol) was taken in TFA (2.5 mL). This clear solution was stirred at room temperature for 60 minutes before concentrated to dryness in vacuuo. This oil was dissolved in 2 mL of 4 N HCl in dioxane and then concentrated to dryness in vacuuo to give the desired product as a white solid (40 mg, 75%). LC-MS for $C_{23}H_{31}F_3N_5OS$ [M+H$^+$]:calculated 482.21, found 482.15.

Step D

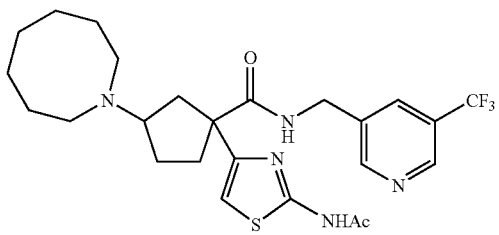

To a solution of the product from Step C (100 mg, 0.208 mmol) in CH$_2$Cl$_2$ (2 mL) was added pyridine (500 µL, 4.16 mmol) followed by AC$_2$O (133 µL, 1.04 mmol). The reaction was stirred at room temperature for 2 hours before quenched by the addition of methanol (0.5 mL). The resulted mixture was purified on preparative TLC plate (10% MeOH/CH$_2$Cl$_2$/ 0.1%NH$_4$OH) to give the desired cis (70 mg, 64% yield) and trans (25 mg, 23% yield) isomers. LC-MS for $C_{25}H_{33}F_3N_5O_2S$ [M+H$^+$]: calculated 524.22, found 524.15.

EXAMPLES 5-9

Examples 5-9 were synthesized according to the procedures described in Example 4 using different substituents at R1 and R2.

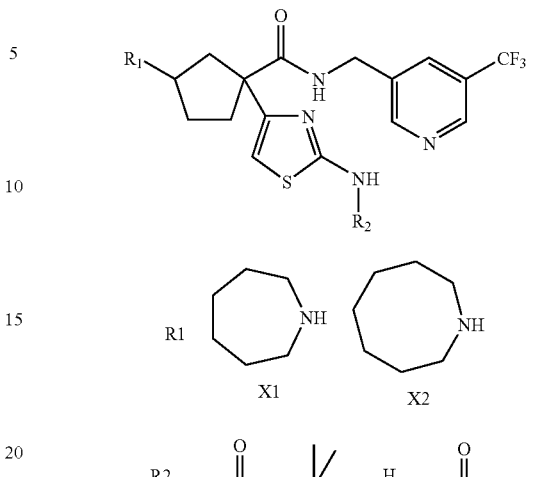

| Example | R1 | R2 | Molecular formula | Calc. MW | [M + H]$^+$ (actual) |
|---|---|---|---|---|---|
| 5 | X1 | Boc | C27H36F3N5O3S | 567.25 | 568.25 |
| 6 | X2 | Boc | C28H38F3N5O3S | 581.26 | 582.35 |
| 7 | X1 | H | C22H28F3N5OS | 467.20 | 468.20 |
| 8 | X2 | H | C23H30F3N5OS | 481.21 | 482.15 |
| 9 | X2 | Ac | C25H32F3N5O2S | 523.22 | 524.15 |

EXAMPLE 10

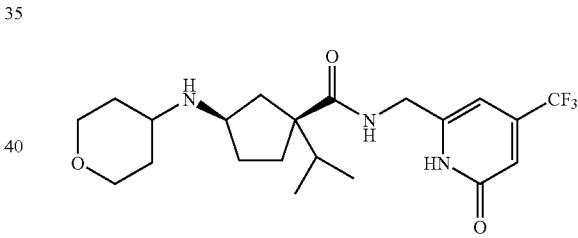

Step A

To a solution of amine Intermediate 1 (150 mg, 0.604 mmol), acid Intermediate 2 (164 mg, 0.604 mmol), 1-hydroxy-7-azabenzitriazole (83 mg, 0.60 mmol) and 1-[3-dimethylamin)opropyl]-3-ethylcarbodiimide (174 mg, 0.906 mmol) in 8 mL of dichloromethane was stirred at room temperature overnight. The reaction was quenched with water, and the product was extracted with dichloromethane (3×20 mL). The combined extracts were dried with magnesium sulfate, and the solvent was removed in vacuo. The residue (299.6 mg) was purified by preparative TLC using a mixture of ethyl acetate/hexane (3:7) as an eluent. This yielded 166.5 mg (55%) of pure material. For $C_{25}H_{38}F_3N_3O_4+H^+-BOC$] calculated 346.17, found 346.15.

Step B

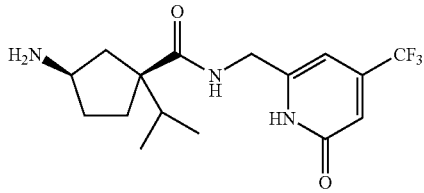

A solution of the tert-Butyl ether 166.5 mg, 0.3321 mmol), the synthesis of which was described in previous step in 8 mL of dichloromethane was treated with 2 mL of trifluoroacetic acid and the resulting reaction mixture was stirred at room temperature for 3 hrs. The solvent was removed in vacuo to yield 157.8 mg (100%) of pure product in a form of a salt with trifluoroacetic acid. For $C_{16}H_{22}F_3N_3O_2+H^+$] calculated 346.17, found 346.10.

Step C

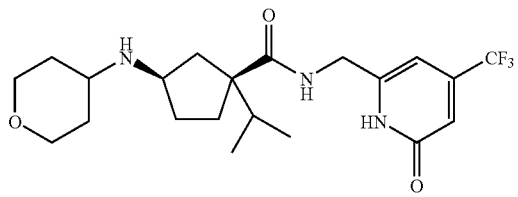

A mixture of the amine from previous step (157 mg, 0.332 mmol), tetrahydropyran-4-one (99.7 mg, 0.996 mmol), crushed 4 A molecular sieves (480 mg), diisopropylethyl amine (58 mg, 0.33 mmol) and sodium triacetoxyborohydride (210 mg, 0.996 mmol) in dichloromethane (8 mL) was stirred overnight. The reaction mixture was diluted with dichloromethane (20 mL), and washed with sat. aq. solution of sodium bicarbonate. The organic layer was evaporated to dryness, and the residue (67 mg) was further purified by preparative HPLC to afford 11.2 mg of desired product. For $C_{21}H_{30}F_3N_3O_3+H^+$] calculated 430.22, found 430.15.

EXAMPLE 11

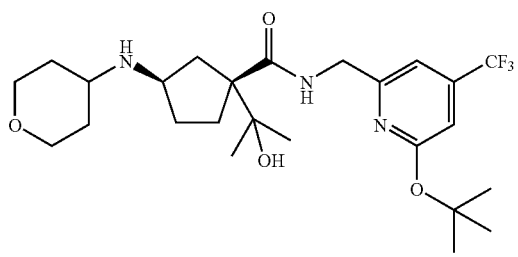

Step A

Procedure A

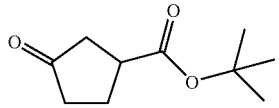

A solution of 3-oxo-cyclopentane carboxylic acid (Stetter, H., Kuhlmann, H. Liebigs Ann. Chem., 1979, 7, 944-9) (5.72 g, 44.6 mmol) in dichloromethane (30 mL) was treated with N,N'-di-iso-propyl-O-tert-Butyl-iso-urea (21.2 mL, 89.3 mmol) and the reaction mixture was stirred at ambient temperature overnight. The precipitated N,N'-di-iso-propyl urea was filtered off, the filtrate concentrated in vacuo and the residue was purified by distillation (b.p.: 125-129° C. @ 18 mmHg) to yield 4.7446 g (58%) of the pure product. $^1$H NMR (500 MHz, CDCl$_3$): 3.02 (p, J=7.8 Hz, 1H), 2.05-2.50 (m, 6H), 1.45 (s, 9H). $^{13}$C NMR (125 MHz, CDCl$_3$): 217.00, 173.47, 80.99, 41.88, 41.14, 27.94, 26.57.

Procedure B

A 2 L round RBF was charged with anhydrous magnesium sulfate (113 g, 940 mmol) and dichloromethane (940 mL). While stirring, the suspension was treated with concentrated sulfuric acid (12.5 mL, 235 mmol) followed after 15 minutes by 3-oxo-cyclopentane carboxylic acid (30.1 g, 235 mmol). After stirring for 15 minutes, tert-butanol (87 g, 1.2 mol) was added. The reaction vessel was closed with a stopper to aid retention of isobutylene, and stirred at ambient temperature for 72 h The solid was filtered off through a plug of Celite and the volume of the filtrate was reduced to approximately 500 mL, and washed with a saturated solution of sodium bicarbonate (2×150 mL). The organic phase was dried with anhydrous magnesium sulfate, filtered, and the solvent was removed by distillation at reduced pressure (180 mmHg). The crude product was purified by distillation to yield 39.12 g (90%) of pure product.

Step B

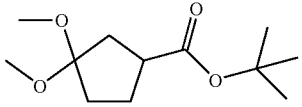

A solution of tert-Butyl 3-oxocyclopentane carboxylate (11.54 g, 62.64 mmol) in dichloromethane (200 mL) was treated with trimethyl orthoformate (41.4 mL, 251 mmol) in the presence of p-toluenesulfonic acid (400 mg) and stirred at room temperature for 48 h. The dark reaction mixture was poured onto a saturated solution of sodium bicarbonate, and the crude product was extracted with dichloromethane. The combined organic extracts were dried with anhydrous magnesium sulfate, the solvent was removed in vacuo, and the crude product was purified by distillation (b.p.: 104° C. @ 4 mmHg) to yield 12.32 g (85%) of the desired product. $^1$H NMR (500 MHz, CDCl$_3$): 3.21 (s, 3H), 3.20 (s, 3H), 2.80 (m, 1H), 2.10 to 1.80 (bm, 6H), 1.46 (s, 9H). $^{13}$C NMR (125 MHz, CDCl$_3$): 174.9, 111.2, 80.3, 67.8, 49.2, 42.5, 37.4, 33.8, 28.3, 22.0.

Step C

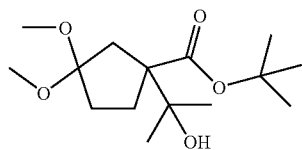

A solution of diisopropylamine (5.6 mL, 40 mmol) in dry tetrahydrofuran (40 mL) was cooled to −78° C. and it was treated with n-butyllithium (16 mL, 40 mmol, 2.5M solution in hexanes). The neat ester from the previous step (5.8 g, 25 mmol) was added via syringe, and the enolate was allowed to form for 30 minutes at −15° C. The temperature of the reaction mixture was lowered to −78° C. once again, and acetone (5.5 mL, 75 mmol) was added via syringe. The reaction was allowed to proceed at −15° C. overnight, and it was quenched by pouring the mixture onto 150 mL of 10% aqueous citric acid. The crude product was extracted into diethyl ether, the combined extracts were dried and the solvent was removed in vacuo. The crude product (8.31 g) was further purified by column chromatography (Silica gel, ethyl acetate+hexanes/ 1:1) to yield 4.31 g (60%) of pure product. $^1$H NMR (500 MHz, CDCl$_3$): 3.21 (s, 3H), 3.18 (s, 3H), 2.46 (d, J=14.2 Hz, 1H), 2.20 (m, 1H), 1.99 (d, J=13.96 Hz), 1.85 (m, 3H), 1.50 (s, 9H), 1.21 (bs, 6H). $^{13}$C NMR (125 MHz, CDCl$_3$): 175.9, 110.4, 81.8, 73.3, 60.6, 49.5, 49.0, 39.5, 33.6, 28.2, 27.9, 26.7, 25.6.

Step D

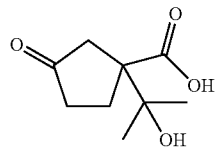

The solution of the ester-acetal (4.31 g, 14.9 mmol) from the previous step in dichloromethane (4 mL) was treated with trifluoroacetic acid (4.0 mL) and stirred at room temperature overnight. The solvent was evaporated in vacuo, and the residue was co distilled several times with hexane to yield 4.14 g of the desired acid. $^1$H NMR (500 MHz, CDCl$_3$): 2.84 (d, J=18.31 Hz), 2.26 (d, J=18.76 Hz), 2.48 to 2.28 (m, 4H), 1.41 (s, 3H), 1.37 (s, 3H).

Step E

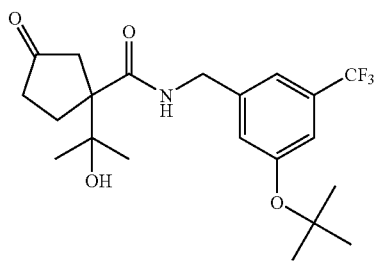

To a solution of amine Intermediate 1 (150 mg, 0.604 mmol), the acid preparation of which was described in the previous step (113 mg, 0.604 mmol), 1-hydroxy-7-azabenzi- triazole (83 mg, 0.604 mmol) and 1-[3-dimethylamin)opropyl]-3-ethylcarbodiimide (174 mg, 0.906 mmol) in 8 mL od dichloromethane was stirred at rt overnight. The reaction was quenched with water, and the product was extracted with dichloromethane (3×20 mL). The combined extracts were dried with magnesium sulfate, and the solvent was removed in vacuo. The residue (306.7 mg) was purified by preparative TLC using a mixture of ethyl acetate/hexane (4:1) as an eluent. This yielded 210 mg (83%) of pure material. For C$_{20}$H$_{27}$F$_3$N$_2$O$_4$+H$^+$−$^t$Bu] calculated 361.17, found 361.15.

Step F

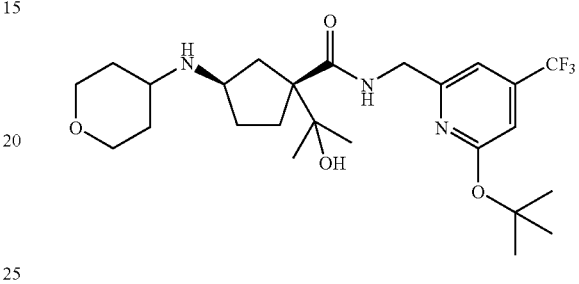

A mixture of the ketone from previous step (210 mg, 0.504 mmol), 4-amino-tetrahydropyrane (138 mg, 1.009 mmol), crushed 4 A molecular sieves (830 mg), diisopropylethyl amine (176 µL 1.008 mmol) and sodium triacetoxyborohydride (320 mg, 1.5 mmol) in dichloromethane (20 mL) was stirred overnight. The intermediate borate was broken down by heating with sat. aq. sodium bicarbonate at 40° C. The crude product was extracted with dichloromethane (3×50 mL), the combined organic layers were dried with anhydrous sodium sulfate, and the solvent was removed in vacuo. The residue (206 mg) was further purified by preparative TLC using a mixture of ethyl acetate+ethanol+aq.ammonium hydroxide (90:8:2) as an eluent to afford 76.1 mg of the desired product. For C$_{25}$H$_{38}$F$_3$N$_3$O$_4$+H$^+$] calculated 502.28, found 502.30. The two respective cis-enantiomeres could be separated into individual enantiomeres using preparative chiral HPLC (Chiralcel OD, eluted with a mixture of hexane-ethanol/98:2, flowrate of 9.0 mL/min, rt, Tr1=18.56 and 20.70 mins, respectively).

EXAMPLE 12

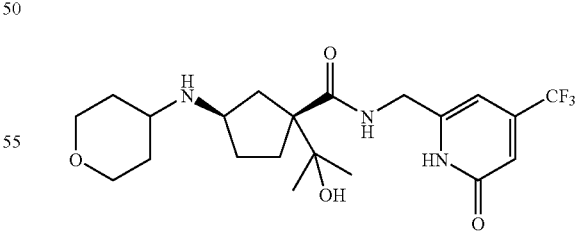

A solution of the enantiomerically pure tert-Butyl ether, preparation of which was described in Example 11, (25 mg, 0.049 mmol) in dichloromethane (6 mL) was treated with trifluoroacetic acid (1 mL) and stirred at room temperature for 1 hr. The solvent was removed in vacuo to afford the clean desired product (19 mg, 86%). For C$_{21}$H$_{30}$F$_3$N$_3$O$_4$+H$^+$] calculated 446.22, found 446.20.

What is claimed is:

1. A compound of the formula I or formula II:

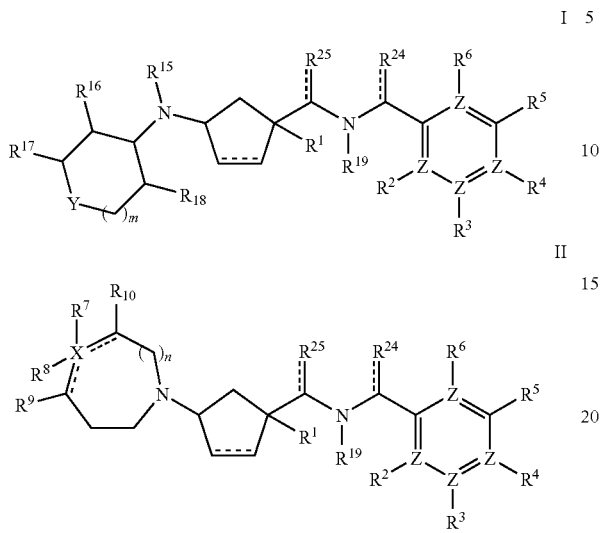

wherein

X is selected from O, N, S, SO$_2$ and C;

Y is selected from —O—, —NR$^{12}$—, —S—, —SO—, —SO$_2$—, and —CR$^{12}$R$^{12}$—, —NSO$_2$R$^{14}$—, —NCOR$^{13}$—, —CR$^{12}$COR$^{11}$—, —CR$^{12}$OCOR$^{13}$—, —CO—;

Z is independently selected from C or N, where at least one Z is N and at most two Z are N;

R$^1$ is selected from: —C$_{1-6}$alkyl, —C$_{0-6}$alkyl-O—C$_{1-6}$alkyl, —C$_{0-6}$alkyl-S—C$_{1-6}$alkyl, —(C$_{0-6}$alkyl)-(C$_{3-7}$cycloalkyl)-(C$_{0-6}$alkyl), hydroxy, heterocycle, —CN, —NR$^{12}$R$^{12}$, —NR$^{12}$COR$^{13}$, —NR$^{12}$SO$_2$R$^{14}$, —COR$^{11}$, —CONR$^{12}$R$^{12}$, phenyl, and pyridyl, where the alkyl and the cycloalkyl are unsubstituted or substituted with 1-7 substituents independently selected from: halo, hydroxy, —O—C$_{1-3}$alkyl, trifluoromethyl, C$_{1-3}$alkyl, —O—C$_{1-3}$alkyl, —COR$^{11}$, —SO$_2$R$^{14}$, —NHCOCH$_3$, —NHSO$_2$CH$_3$, -heterocycle, =O, —CN, where the phenyl and pyridyl are unsubstituted or substituted with 1-3 substituents where the substituents are independently selected from: halo, hydroxy, COR$^{11}$, C$_{1-3}$alkyl, C$_{1-3}$alkoxy and trifluoromethyl;

where R$^{11}$ is independently selected from: hydroxy, hydrogen, C$_{1-6}$ alkyl, —O—C$_{1-6}$alkyl, benzyl, phenyl and C$_{3-6}$ cycloalkyl, where the alkyl, phenyl, benzyl, and cycloalkyl groups are unsubstituted or substituted with 1-3 substituents independently selected from: halo, hydroxy, C$_{1-3}$alkyl, C$_{1-3}$alkoxy, —CO$_2$H, —CO$_2$—C$_{1-6}$ alkyl, and trifluoromethyl, where R$^{12}$ is selected from: hydrogen, C$_{1-6}$ alkyl, benzyl, phenyl and C$_{3-6}$ cycloalkyl, where the alkyl, phenyl, benzyl, and cycloalkyl groups are unsubstituted or substituted with 1-3 substituents independently selected from: halo, hydroxy, C$_{1-3}$alkyl, C$_{1-3}$alkoxy, —CO$_2$H, —CO$_2$—C$_{1-6}$alkyl, and trifluoromethyl, where R$^{13}$ is selected from: hydrogen, C$_{1-6}$ alkyl, —O—C$_{1-6}$alkyl, benzyl, phenyl and C$_{3-6}$ cycloalkyl, where the alkyl, phenyl, benzyl, and cycloalkyl groups are unsubstituted or substituted with 1-3 substituents independently selected from: halo, hydroxy, C$_{1-3}$alkyl, C$_{1-3}$alkoxy, —CO$_2$H, —CO$_2$—C$_{1-6}$alkyl, and trifluoromethyl, and where R$^{14}$ is selected from: hydroxy, C$_{1-6}$ alkyl, —O—C$_{1-6}$alkyl, benzyl, phenyl and C$_{3-6}$ cycloalkyl, where the alkyl, phenyl, benzyl, and cycloalkyl groups are unsubstituted or substituted with 1-3 substituents independently selected from: halo, hydroxy, C$_{1-3}$alkyl, C$_{1-3}$alkoxy, —CO$_2$H, —CO$_2$—C$_{1-6}$ alkyl, and trifluoromethyl;

R$^2$ is selected from: hydrogen, C$_{1-3}$alkyl, unsubstituted or substituted with 1-3 fluoro, —O—C$_{1-6}$alkyl, unsubstituted or substituted with 1-3 fluoro, hydroxy, chloro, fluoro, bromo, phenyl, heterocycle, and nothing, and O, when the Z bonded to R$^2$ is N;

R$^3$ is selected from: hydrogen, C$_{1-3}$alkyl, unsubstituted or substituted with 1-3 fluoro, —O—C$_{1-3}$alkyl, unsubstituted or substituted with 1-3 fluoro, hydroxy, chloro, fluoro, bromo, phenyl, heterocycle, and nothing, and O, when the Z bonded to R$^2$ is N;

R$^4$ is selected from: hydrogen, C$_{1-3}$alkyl, unsubstituted or substituted with 1-3 fluoro, —O—C$_{1-3}$alkyl, unsubstituted or substituted with 1-3 fluoro, hydroxy, chloro, fluoro, bromo, phenyl, heterocycle, and nothing, and O, when the Z bonded to R$^2$ is N;

R$^5$ is selected from: C$_{1-6}$alkyl, unsubstituted or substituted with 1-6 substituents selected from fluoro and hydroxyl, —O—C$_{1-6}$alkyl, unsubstituted or substituted with 1-6 fluoro, —CO—C$_{1-6}$alkyl, unsubstituted or substituted with 1-6 fluoro, —S—C$_{1-6}$alkyl, unsubstituted or substituted with 1-6 fluoro, -pyridyl, unsubstituted or substituted with one or more substituents selected from: halo, trifluoromethyl, C$_{1-4}$alkyl, and COR$^{11}$, fluoro, chloro, bromo, —C$_{4-6}$cycloalkyl, —O—C$_{4-6}$cycloalkyl, phenyl, unsubstituted or substituted with one or more substituents selected from: halo, trifluoromethyl, C$_{1-4}$alkyl, and COR$^{11}$, —O-phenyl, unsubstituted or substituted with one or more substituents selected from: halo, trifluoromethyl, C$_{1-4}$alkyl, and COR$^{11}$, —C$_{3-6}$cycloalkyl, unsubstituted or substituted with 1-6 fluoro, —O—C$_{3-6}$cycloalkyl, unsubstituted or substituted with 1-6 fluoro, -heterocycle, —CN, and —COR$^{11}$;

R$^6$ is selected from: hydrogen, C$_{1-3}$alkyl, unsubstituted or substituted with 1-3 fluoro, —O—C$_{1-3}$alkyl, unsubstituted or substituted with 1-3 fluoro, hydroxy, chloro, fluoro, bromo, phenyl, heterocycle, and nothing, and O, when the Z bonded to R$^2$ is N;

R$^7$ is selected from: hydrogen, (C$_{0-6}$alkyl)-phenyl, (C$_{0-6}$alkyl)-heterocycle, (C$_{0-6}$alkyl)-C$_{3-7}$cycloalkyl, (C$_{0-6}$alkyl)-COR$^{11}$, (C$_{0-6}$alkyl)-(alkene)-COR$^{11}$, (C$_{0-6}$alkyl)-SO$_3$H, (C$_{0-6}$alkyl)-W—C$_{0-4}$alkyl, (C$_{0-6}$alkyl)-CONR$^{12}$-phenyl, (C$_{0-6}$alkyl)-CONR$^{20}$—V—COR$^{11}$, and nothing, when X is O, S, or SO$_2$, where W is selected from: a single bond, —O—, —S—, —SO—, —SO$_2$—, —CO—, —CO$_2$—, —CONR$^{12}$— and —NR$^{12}$—, where V is selected from C$_{1-6}$alkyl or phenyl, where R$^{20}$ is hydrogen or C$_{1-4}$alkyl, or where R$^{20}$ is joined via a 1-5 carbon tether to one of the carbons of V to form a ring, where the C$_{0-6}$alkyl is unsubstituted or substituted with 1-5 substituents independently selected from: halo, hydroxy, —C$_{0-6}$alkyl, —O—C$_{1-3}$alkyl, trifluoromethyl, and —C$_{0-2}$alkyl-phenyl, where the phenyl, heterocycle, cycloalkyl, and C$_{0-4}$alkyl is unsubstituted or substituted with 1-5 substituents independently selected from: halo, trifluoromethyl, hydroxy, $C_{1-3}$alkyl, —O—$C_{1-3}$alkyl, —$C_{0-3}$—$COR^{11}$, —CN, —$NR^{12}R^{12}$, —$CONR^{12}R^{12}$, and —$C_{0-3}$-heterocycle, or where the phenyl and heterocycle may be fused to another heterocycle, which itself may be unsubstituted or substituted with 1-2 substituents independently selected from hydroxy, halo, —$COR^{11}$, and —$C_{1-3}$alkyl, and where alkene is unsubstituted or substituted with 1-3 substituents which are independently selected from: halo, trifluoromethyl, $C_{1-3}$alkyl, phenyl, and heterocycle;

$R^8$ is selected from: hydrogen, nothing when X is either O, S, $SO_2$ or N or when a double bond joins the carbons to which $R^7$ and $R^{10}$ are attached, hydroxy, $C_{1-6}$alkyl, $C_{1-6}$alkyl-hydroxy, —O—$C_{1-3}$alkyl, —$COR^{11}$, —$CONR^{12}R^{12}$, and —CN;

where $R^7$ and $R^8$ may be joined together to form a ring selected from: 1H-indene, 2,3-dihydro-1H-indene, 2,3-dihydro-benzofuran, 1,3-dihydro-isobenzofuran, 2,3-dihydro-benzothiofuran, 1,3-dihydro-isobenzothiofuran, 6H-cyclopenta[d]isoxazol-3-ol, cyclopentane, and cyclohexane, where the ring formed is unsubstituted or substituted with 1-5 substituents independently selected from: halo, trifluoromethyl, hydroxy, $C_{1-3}$alkyl, —O—$C_{1-3}$alkyl, —$C_{0-3}$—$COR^{11}$, —CN, —$NR^{12}R^{12}$, —$CONR^{12}R^{12}$, and —$C_{0-3}$-heterocycle, or where $R^7$ and $R^9$ or $R^8$ and $R^{10}$ may be joined together to form a ring which is phenyl or heterocycle, wherein the ring is unsubstituted or substituted with 1-7 substituents where the substituents are independently selected from: halo, trifluoromethyl, hydroxy, $C_{1-3}$alkyl, —O—$C_{1-3}$alkyl, —$COR^{11}$, —CN, —$NR^{12}R^{12}$, and —$CONR^{12}R^{12}$;

$R^9$ and $R^{10}$ are independently selected from: hydrogen, hydroxy, $C_{1-6}$alkyl, $C_{1-6}$alkyl-$COR^{11}$, $C_{1-6}$alkyl-hydroxy, —O—$C_{1-3}$alkyl, =O, when $R^9$ or $R^{10}$ is connected to the ring via a double bond, and halo;

$R^{15}$ is selected from: hydrogen, and $C_{1-6}$alkyl, unsubstituted or substituted with 1-3 substituents independently selected from: halo, hydroxy, —$CO_2H$, —$CO_2C_{1-6}$alkyl, and —O—$C_{1-3}$alkyl;

$R^{16}$ is selected from: hydrogen, $C_{1-6}$alkyl, unsubstituted or substituted with 1-6 substituents selected from: fluoro, $C_{1-3}$alkoxy, hydroxyl and —$COR^{11}$, fluoro, —O—$C_{1-3}$alkyl, unsubstituted or substituted with 1-3 fluoro, $C_{3-6}$cycloalkyl, —O—$C_{3-6}$cycloalkyl, hydroxy, —COR11, and —$OCOR^{13}$, or $R^{15}$ and $R^{16}$ are joined together via a $C_{2-4}$alkyl or a $C_{0-2}$alkyl-O-$C_{1-3}$alkyl chain to form a 5-7 membered ring;

$R^{17}$ is selected from: hydrogen, $C_{1-6}$alkyl, unsubstituted or substituted with 1-6 substituents selected from: fluoro, $C_{1-3}$alkoxy, hydroxyl and —$COR^{11}$, $COR^{11}$, hydroxy, and —O—$C_{1-6}$alkyl, unsubstituted or substituted with 1-6 substituents selected form: fluoro, $C_{1-3}$alkoxy, hydroxy, and —$COR^{11}$, or $R^{16}$ and $R^{17}$ may be joined together by a $C_{1-4}$alkyl chain or a $C_{0-3}$alkyl-O—$C_{0-3}$alkyl chain to form a 3-6 membered ring;

$R^{18}$ is selected from: hydrogen, $C_{1-6}$alkyl, unsubstituted or substituted with 1-6 fluoro, fluoro, —O—$C_{3-6}$cycloalkyl, and —O—$C_{1-3}$alkyl, unsubstituted or substituted with 1-6 fluoro, or $R^{16}$ and $R^{18}$ are joined together by a $C_{2-3}$alkyl chain to form a 5-6 membered ring, where the alkyl are unsubstituted or substituted with 1-3 substituents independently selected from: halo, hydroxy, —$COR^{11}$, $C_{1-3}$alkyl, and $C_{1-3}$alkoxy, or $R^{16}$ and $R^{18}$ are joined together by a $C_{1-2}$alkyl-O-$C_{1-2}$alkyl chain to form a 6-8 membered ring, where the alkyl are unsubstituted or substituted with 1-3 substituents independently selected from: halo, hydroxy, —$COR^{11}$, $C_{1-3}$alkyl, and $C_{1-3}$alkoxy, or $R^{16}$ and $R^{18}$ are joined together by a —O—$C_{1-2}$alkyl-O— chain to form a 6-7 membered ring, where the alkyl are unsubstituted or substituted with 1-3 substituents independently selected from: halo, hydroxy, —$COR^{11}$, $C_{1-3}$alkyl, and $C_{1-3}$alkoxy;

$R^{19}$ is selected from: hydrogen, phenyl, $C_{1-6}$alkyl substituted or unsubstituted with 1-6 substituents selected from: —$COR^{11}$, hydroxy, fluoro, chloro and —O—$C_{1-3}$alkyl;

$R^{24}$ and $R^{25}$ are independently selected from: =O, where one of $R^{24}$ and $R^{25}$ is oxygen bound via a double bond hydrogen, phenyl, and $C_{1-6}$alkyl, substituted or unsubstituted with 1-6 substituents selected from: —$COR^{11}$, hydroxy, fluoro, chloro, —O—$C_{1-3}$alkyl;

m is 0, 1 or 2;

n is 1 or 2;

the dashed line represents a single or a double bond;

and pharmaceutically acceptable salts thereof and individual diastereomers thereof.

2. The compound of claim 1 of the formula Ia:

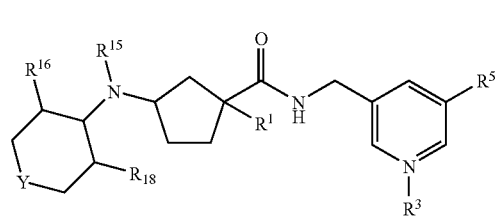

Ia and pharmaceutically acceptable salts and individual diastereomers thereof.

3. The compound of claim 1 of the formula IIa:

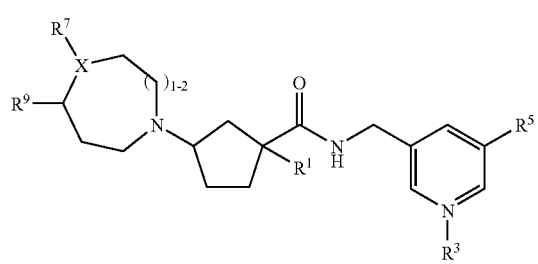

IIa and pharmaceutically acceptable salts and individual diastereomers thereof.

4. The compound of claim 1 of the formula Ib:

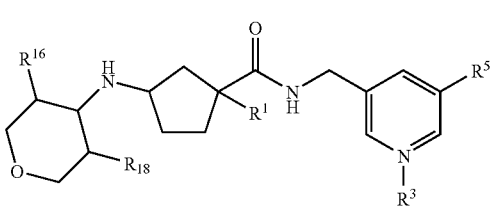

and pharmaceutically acceptable salts and individual diastereomers thereof.

5. The compound of claim 1 of the formula IIb:

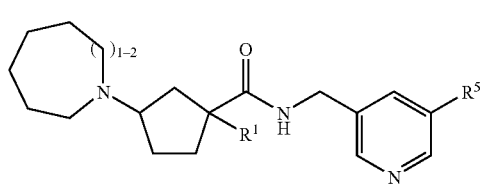

and pharmaceutically acceptable salts and individual diastereomers thereof.

6. The compound of claim 1 of the formula Ic:

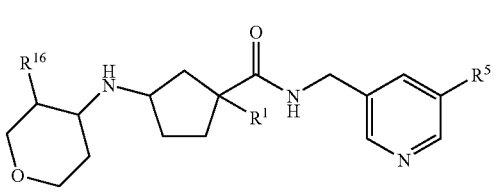

and pharmaceutically acceptable salts and individual diastereomers thereof.

7. The compound of claim 1, wherein X is C, O or N.

8. The compound of claim 1, wherein X is C.

9. The compound of claim 1, wherein Y is —$CH_2$— or —O—.

10. The compound of claim 1, wherein $R^1$ is selected from: —$C_{1-6}$alkyl, —$C_{0-6}$alkyl-O-$C_{1-6}$alkyl, heterocycle, and —($C_{0-6}$alkyl)-($C_{3-7}$cycloalkyl)-($C_{0-6}$alkyl), where the alkyl, heterocycle, and the cycloalkyl are unsubstituted or substituted with 1-7 substituents independently selected from: halo, hydroxy, —O—$C_{1-3}$alkyl, trifluoromethyl, $C_{1-3}$alkyl, —O—$C_{1-3}$alkyl, —$COR^{11}$, —CN, —$NR^{12}R^{12}$, and —$CONR^{12}R^{12}$.

11. The compound of claim 1, wherein $R^1$ is selected from: —$C_{1-6}$alkyl, unsubstituted or substituted with 1-6 substituents independently selected from: halo, hydroxy, —O—$C_{1-3}$alkyl, trifluoromethyl, and —$COR^{11}$; —$C_{0-6}$alkyl-O—$C_{1-6}$alkyl-, unsubstituted or substituted with 1-6 substituents independently selected from: halo, trifluoromethyl, and —$COR^{11}$; and —($C_{3-5}$cycloalkyl)-($C_{0-6}$alkyl), unsubstituted or substituted with 1-7 substituents independently selected from: halo, hydroxy, —O—$C_{1-3}$alkyl, trifluoromethyl, and —$COR^{11}$.

12. The compound of claim 1, wherein $R^1$ is selected from: $C_{1-6}$alkyl, $C_{1-6}$alkyl substituted with hydroxyl, and $C_{1-6}$alkyl substituted with 1-6 fluoro.

13. The compound of claim 1, wherein $R^1$ is selected from: —$CH(CH_3)_2$, —$CH(OH)CH_3$, —$C(OH)(CH_3)_2$, and —$CH_2CF_3$.

14. The compound of claim 1, wherein $R^2$ is hydrogen.

15. The compound of claim 1, wherein $R^3$ is nothing.

16. The compound of claim 1, wherein $R^4$ is hydrogen.

17. The compound of claim 1, wherein $R^5$ is selected from: $C_{1-6}$alkyl substituted with 1-6 fluoro, —O—$C_{1-6}$alkyl substituted with 1-6 fluoro, chloro, bromo, and phenyl.

18. The compound of claim 1, wherein which $R^5$ is selected from: trifluoromethyl, trifluoromethoxy, chloro, bromo, and phenyl.

19. The compound of claim 1, wherein $R^5$ is trifluoromethyl.

20. The compound of claim 1, wherein $R^6$ is hydrogen.

21. The compound of claim 1, wherein $R^7$ is selected from phenyl, heterocycle, $C_{3-7}$cycloalkyl, $C_{1-6}$alkyl, —$COR^{11}$, and —CONH—V—$COR^{11}$, where V is selected from $C_{1-6}$alkyl and phenyl, and where the phenyl, heterocycle, $C_{3-7}$cycloalkyl, and $C_{1-6}$alkyl is unsubstituted or substituted with 1-5 substituents independently selected from: halo, trifluoromethyl, hydroxy, $C_{1-3}$alkyl, —O—$C_{1-3}$alkyl, —$COR^{11}$, —CN, -heterocycle, and —$CONR^{12}R^{12}$.

22. The compound of claim 1, wherein, when X is not O, $R^7$ is selected from phenyl, heterocycle, $C_{1-4}$alkyl, —$COR^{11}$ and —CONH—V—$COR^{11}$, where V is selected from $C_{1-6}$alkyl or phenyl, where the phenyl, heterocycle, and $C_{1-4}$alkyl is unsubstituted or substituted with 1-3 substituents independently selected from: halo, hydroxy, $C_{1-3}$alkyl, —O—$C_{1-3}$alkyl, —$COR^{11}$, and -heterocycle.

23. The compound of claim 1, wherein X is O, and $R^7$ and $R^8$ are nothing.

24. The compound of claim 1, wherein X is C, and $R^8$ is hydrogen.

25. The compound of claim 1, wherein which $R^9$ is selected from: hydrogen, hydroxy, —$CH_3$, —O—$CH_3$, and =O, where $R^9$ is joined to the ring via a double bond.

26. The compound of claim 1, wherein $R^9$ is hydrogen.

27. The compound of claim 1, wherein $R^{10}$ is hydrogen.

28. The compound of claim 1, wherein $R^{15}$ is hydrogen or methyl.

29. The compound of claim 1, wherein $R^{16}$ is selected from: hydrogen, $C_{1-3}$alkyl, unsubstituted or substituted with 1-6 fluoro, —O—$C_{1-3}$alkyl, fluoro, and hydroxy.

30. The compound of claim 1, wherein $R^{16}$ is selected from: hydrogen, trifluoromethyl, methyl, methoxy, ethoxy, ethyl, fluoro, and hydroxy.

31. The compound of claim 1, wherein $R^{17}$ is hydrogen.

32. The compound of claim 1, wherein $R^{18}$ is selected from: hydrogen, methyl, and methoxy.

33. The compound of claim 1, wherein $R^{18}$ is hydrogen.

34. The compound of claim 1, wherein $R^{16}$ and $R^{18}$ are joined together by a —$CH_2CH_2$— chain or a —$CH_2CH_2CH_2$— chain to form a cyclopentyl ring or a cyclohexyl ring.

35. The compound of claim 1, wherein $R^{19}$ is hydrogen.

36. The compound of claim 1, wherein $R^{24}$ is hydrogen.

37. The compound of claim 1, wherein $R^{25}$ is =O.

38. The compound of claim 1, wherein m=0 or 1.

39. The compound of claim 1, wherein n=1 or 2.

40. A compound selected from:
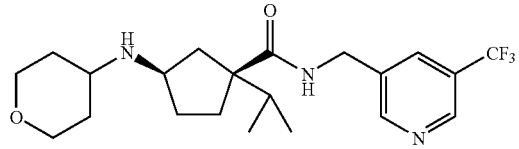
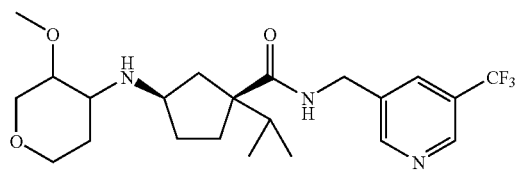
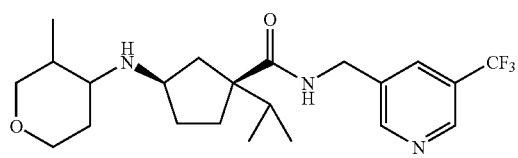
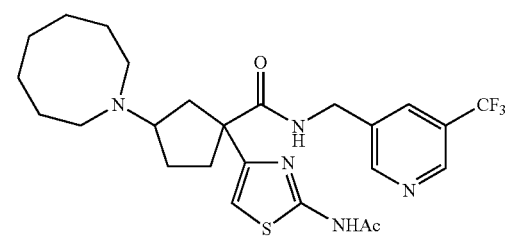
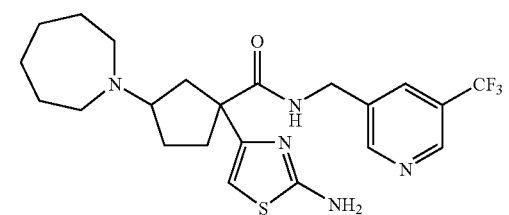
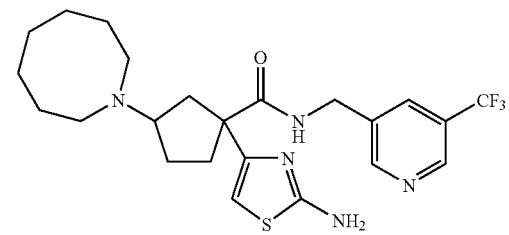
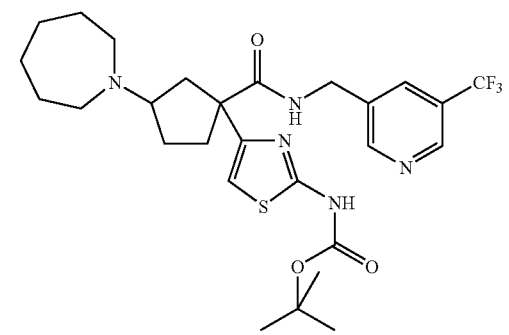
-continued
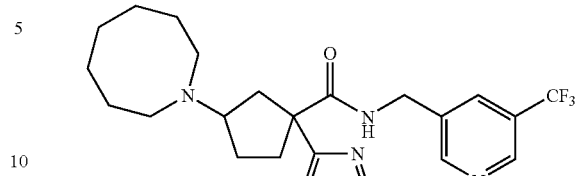
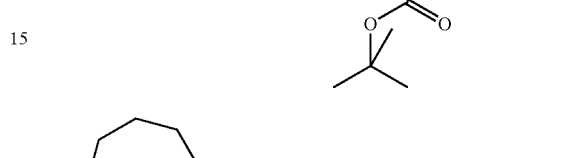
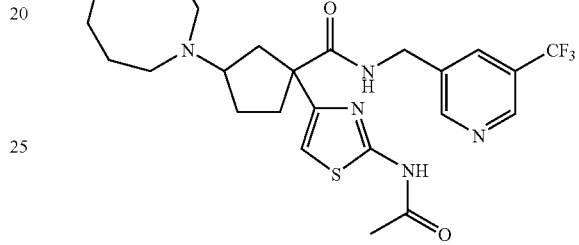
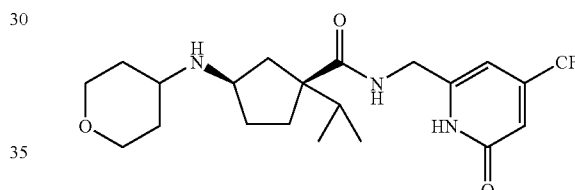
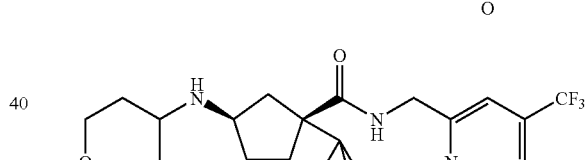
41. A pharmaceutical composition which comprises an inert carrier and a compound of claim 1.
42. A method for treating rheumatoid arthritis which comprises the administration to a patient of an effective amount of a compound of claim 1.
\* \* \* \* \*